United States Patent
Tibbatts et al.

(12) 
(10) Patent No.: US 10,716,904 B2
(45) Date of Patent: Jul. 21, 2020

(54) DRY POWDER INHALER

(71) Applicant: Philip Morris Products S.A., Neuchatel (CH)

(72) Inventors: James Tibbatts, Cambridge (GB); Robin Craig Cocker, Derby (GB); Ben Alexander King, Peterborough (GB); Christopher Iain Davidson, Cambridge (GB); Paul Mutti, Lincolnshire (GB); Alex Stenzler, Long Beach, CA (US); Steve Han, Huntington Beach, CA (US)

(73) Assignee: Philip Morris Products S.A., Neuchatel (CH)

( * ) Notice: Subject to any disclaimer, the term of this patent is extended or adjusted under 35 U.S.C. 154(b) by 299 days.

(21) Appl. No.: 15/646,205

(22) Filed: Jul. 11, 2017

(65) Prior Publication Data

US 2018/0021529 A1 Jan. 25, 2018

Related U.S. Application Data

(60) Provisional application No. 62/365,201, filed on Jul. 21, 2016, provisional application No. 62/450,327, filed on Jan. 25, 2017.

(51) Int. Cl.
*A61M 15/00* (2006.01)
*A61M 11/00* (2006.01)
*A61M 15/06* (2006.01)

(52) U.S. Cl.
CPC ...... *A61M 15/0008* (2014.02); *A61M 11/003* (2014.02); *A61M 15/0026* (2014.02);
(Continued)

(58) Field of Classification Search
CPC ........... A61M 13/00–005; A61M 11/001–003; A61M 15/06; A61M 15/0005;
(Continued)

(56) References Cited

U.S. PATENT DOCUMENTS

| | | | | | |
|---|---|---|---|---|---|
| 5,575,280 | A | * | 11/1996 | Gupte | A61M 15/0065 128/203.15 |
| 5,702,362 | A | * | 12/1997 | Herold | A61M 15/0065 604/58 |

(Continued)

FOREIGN PATENT DOCUMENTS

| WO | WO 92/11051 A1 | 7/1992 | |
|---|---|---|---|
| WO | WO-0211801 A1 * | 2/2002 | ........ A61M 15/0065 |
| WO | WO 2007/107431 A1 | 9/2007 | |

OTHER PUBLICATIONS

International Preliminary Report on Patentability for PCT/US2017/041445, issued by the U.S. Patent and Trademark Office as the Search Authority, dated Aug. 10, 2018; 17 pgs.

(Continued)

*Primary Examiner* — Kendra D Carter
*Assistant Examiner* — Thomas W Greig
(74) *Attorney, Agent, or Firm* — Mueting Raasch Group

(57) ABSTRACT

The present invention provides in part dry powder inhaler (DPI) devices for dispensing dry powder and methods for using the same. The DPI devices feature exchangeable cartridges having drum mechanisms that prepare metered doses of dry powder, and are able to direct air in a turbulent manner sufficient to entrain and deagglomerate a dose of dry powder for delivery into a user's lungs. The DPI devices feature a reservoir of dry powder advanced by a plunger, as well as a gauge that advances with the plunger to indicate the amount of dry powder remaining in the reservoir.

20 Claims, 34 Drawing Sheets

(52) U.S. Cl.
CPC .... *A61M 15/0065* (2013.01); *A61M 15/0071* (2014.02); *A61M 15/0076* (2014.02); *A61M 15/06* (2013.01); *A61M 2202/064* (2013.01); *A61M 2205/123* (2013.01); *A61M 2205/583* (2013.01); *A61M 2205/6081* (2013.01); *A61M 2206/16* (2013.01)

(58) Field of Classification Search
CPC ........ A61M 15/0008; A61M 15/00021; A61M 15/005; A61M 15/0026; A61M 15/0025
See application file for complete search history.

(56) References Cited

U.S. PATENT DOCUMENTS

| | | | | |
|---|---|---|---|---|
| 5,996,577 | A * | 12/1999 | Ohki | A61M 15/0065 128/203.12 |
| 6,234,169 | B1 | 5/2001 | Bulbrook | |
| 7,207,330 | B1 * | 4/2007 | Braithwaite | A61M 15/0065 128/203.15 |
| 7,854,226 | B2 * | 12/2010 | Pinon | A61M 15/0065 128/203.15 |
| 2001/0020147 | A1 * | 9/2001 | Staniforth | A61M 15/0066 604/58 |
| 2003/0123921 | A1 | 7/2003 | Abbas | |
| 2004/0089298 | A1 | 5/2004 | Haikarainen et al. | |
| 2004/0107963 | A1 * | 6/2004 | Finlay | A61M 15/0086 128/203.15 |
| 2004/0123865 | A1 * | 7/2004 | Haikarainen | A61M 15/0065 128/203.15 |
| 2005/0183723 | A1 | 8/2005 | Pinon et al. | |
| 2006/0180148 | A1 * | 8/2006 | Beller | A61M 15/0065 128/203.15 |
| 2009/0025721 | A1 | 1/2009 | Ellwanger et al. | |
| 2010/0012120 | A1 | 1/2010 | Herder et al. | |
| 2010/0300441 | A1 * | 12/2010 | Von Schuckmann | A61M 15/0065 128/203.15 |
| 2011/0162642 | A1 | 7/2011 | Akouka et al. | |
| 2015/0343159 | A1 | 12/2015 | Farr et al. | |
| 2017/0203056 | A1 * | 7/2017 | Dunne | B05B 11/0054 |

OTHER PUBLICATIONS

International Search Report and Written Opinion for PCT/US2017/041445, issued by the U.S. Patent and Trademark Office as the Search Authority, dated Sep. 27, 2017; 9 pgs.

Extended EP Search Report for corresponding EP application EP 17831572.7; issued by the European Patent Office dated Feb. 7, 2020; 8 pgs.

* cited by examiner

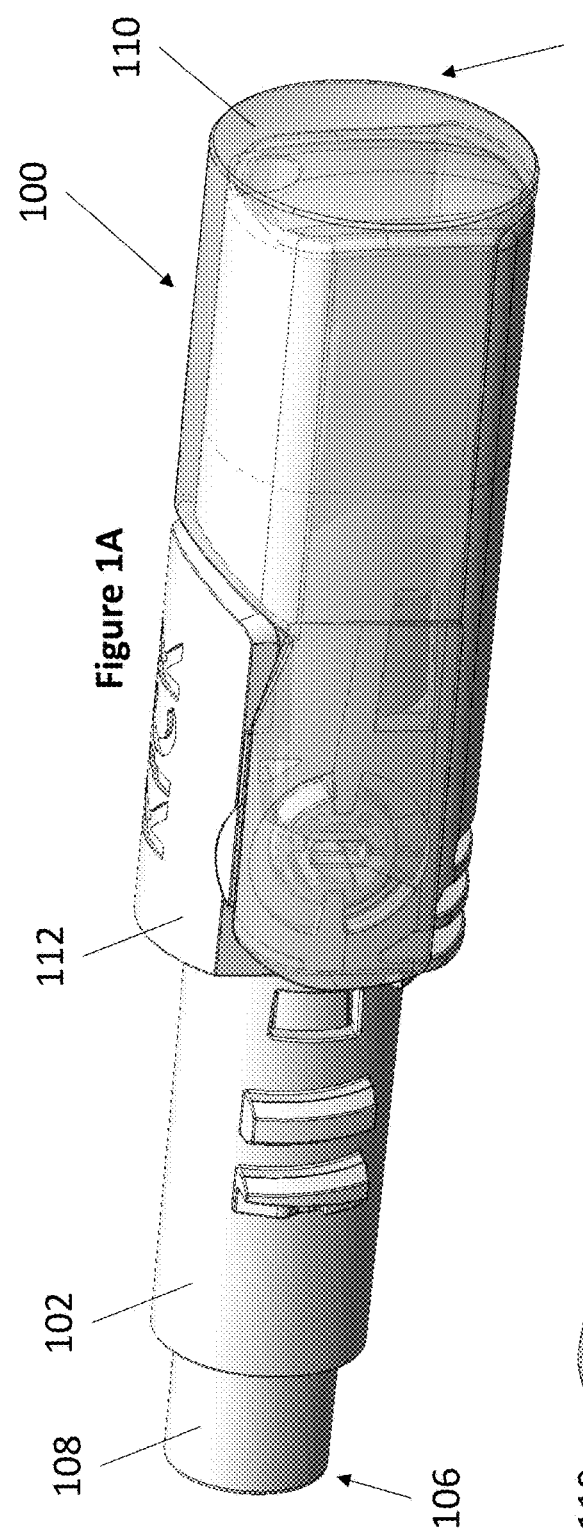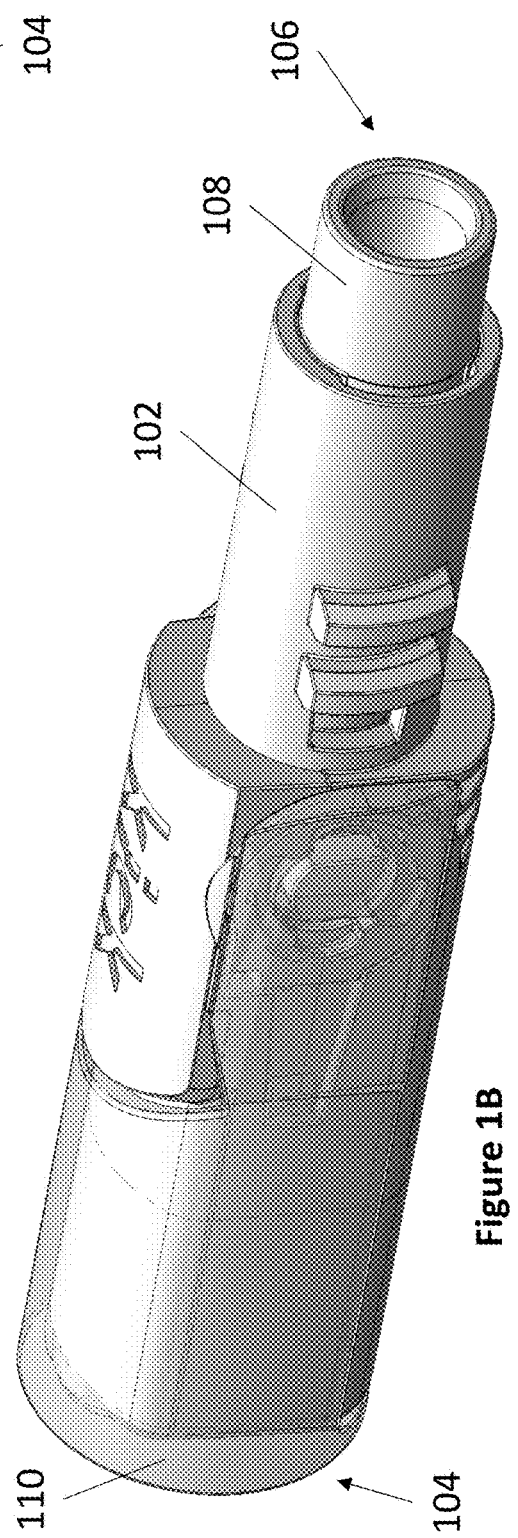
Figure 1A
Figure 1B
Figure 1A – Figure 1B

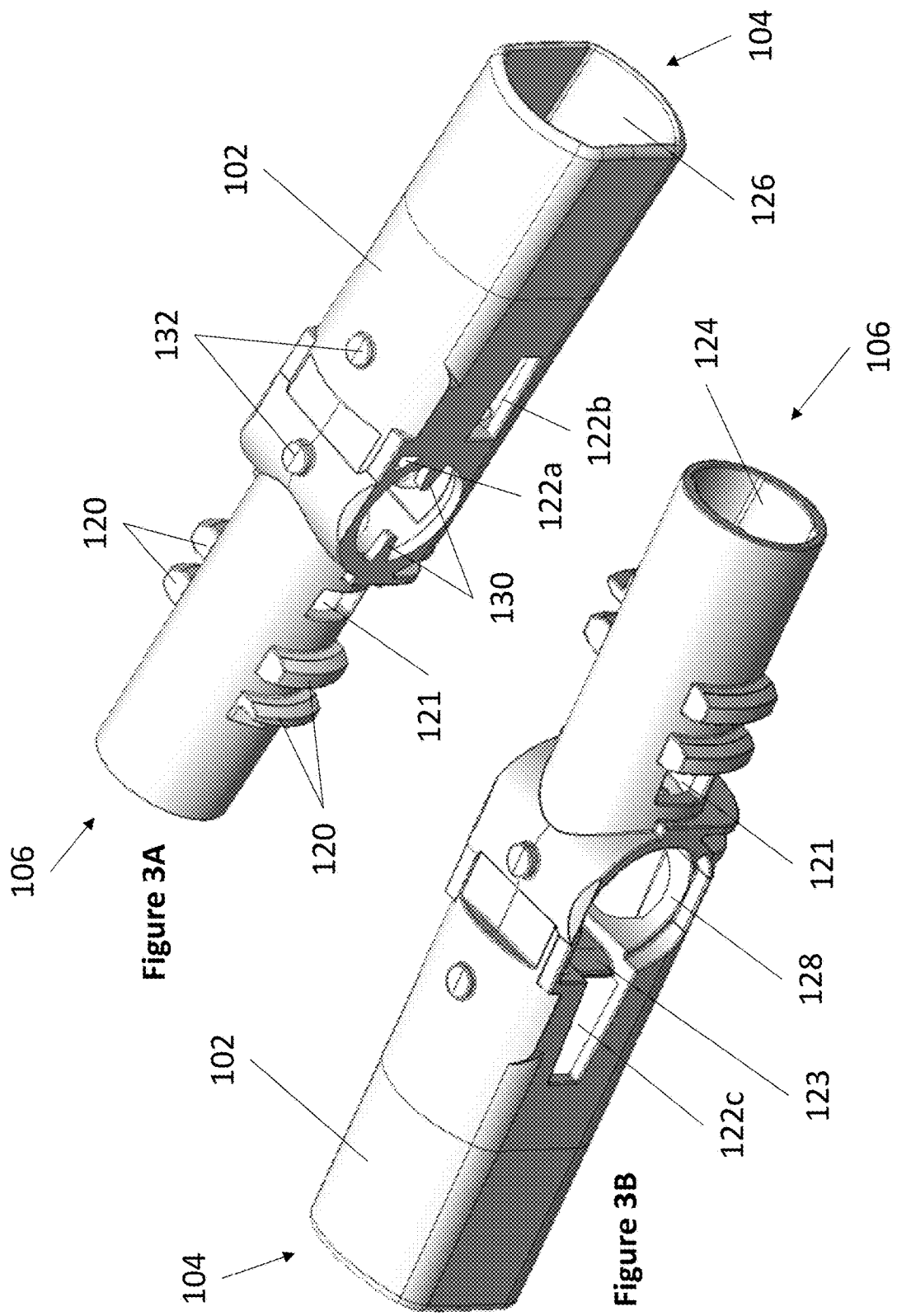

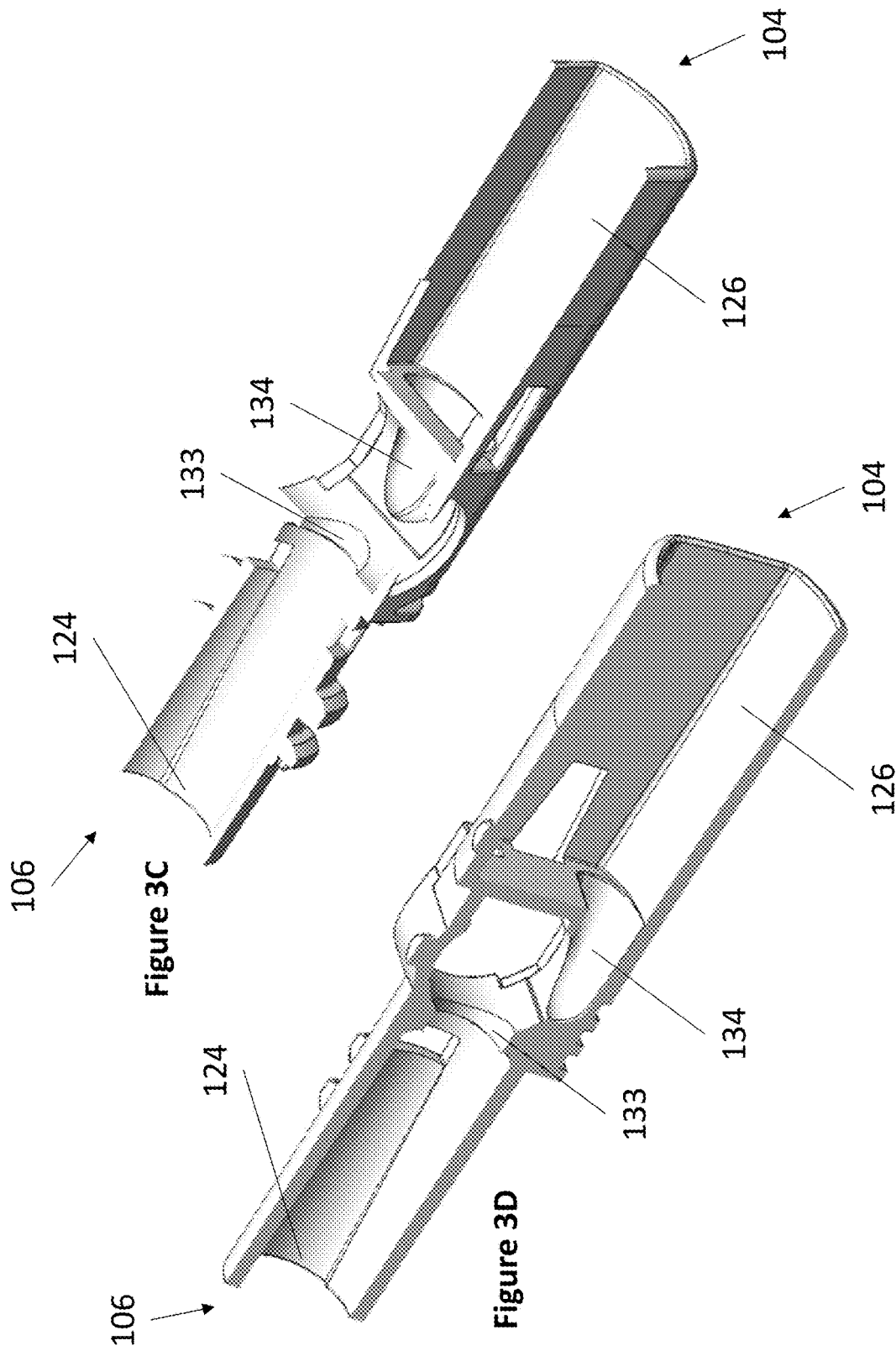

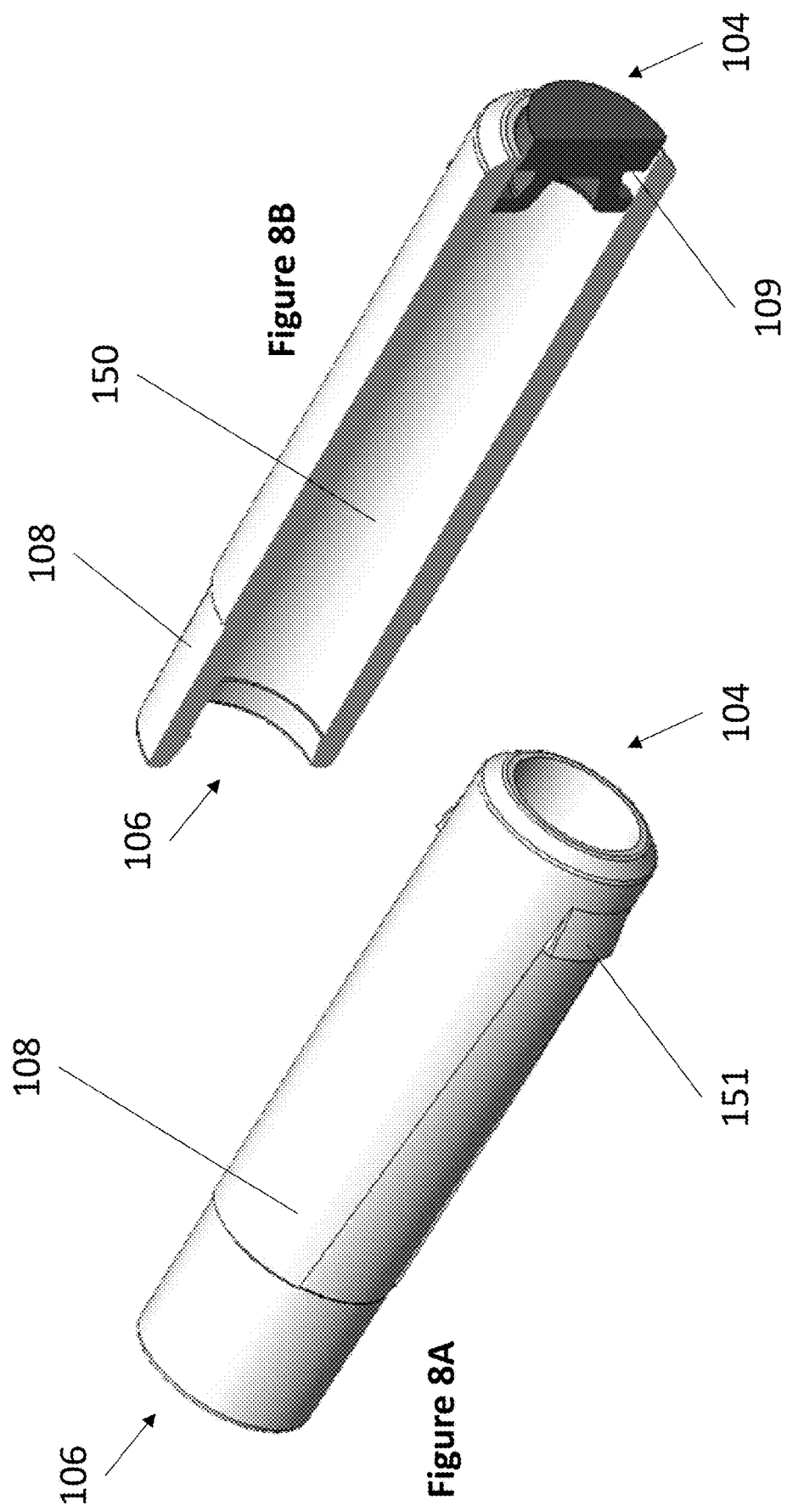

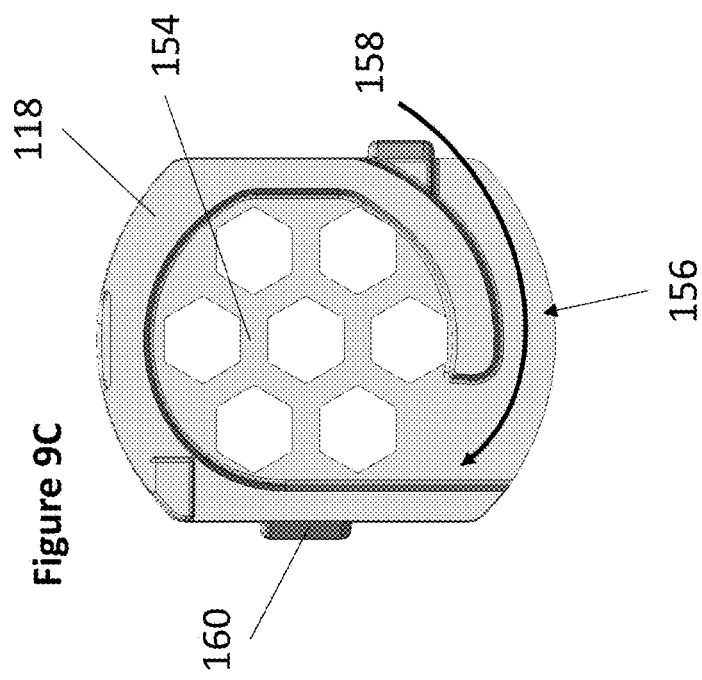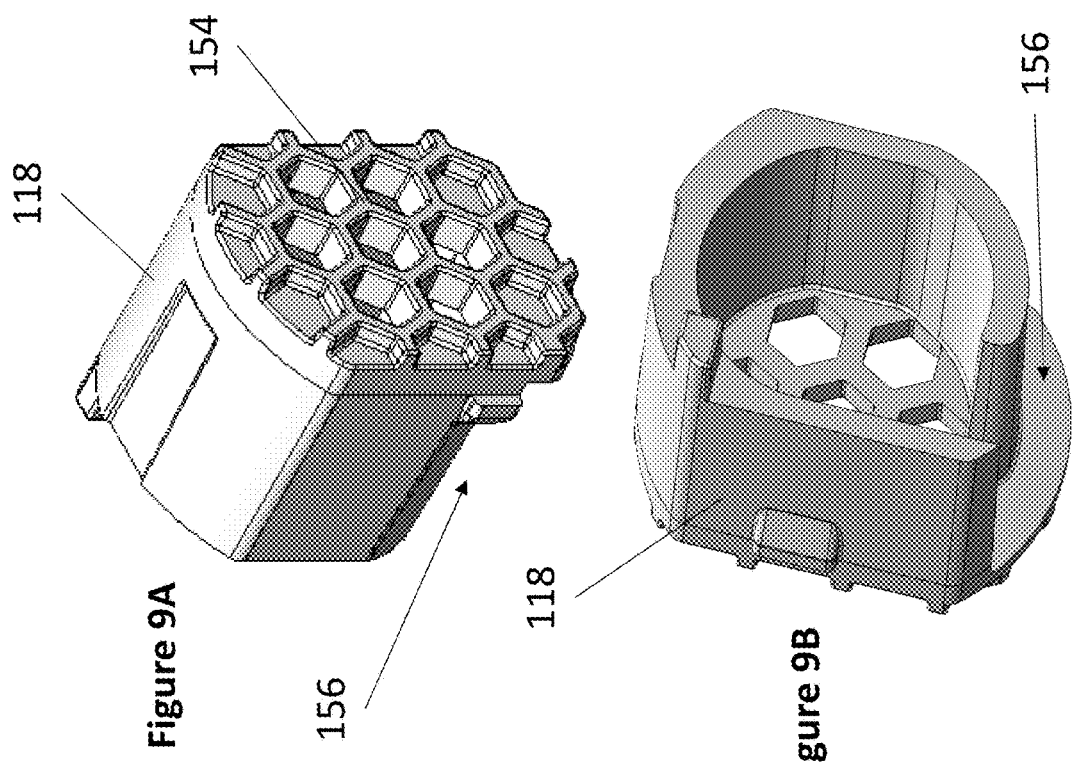

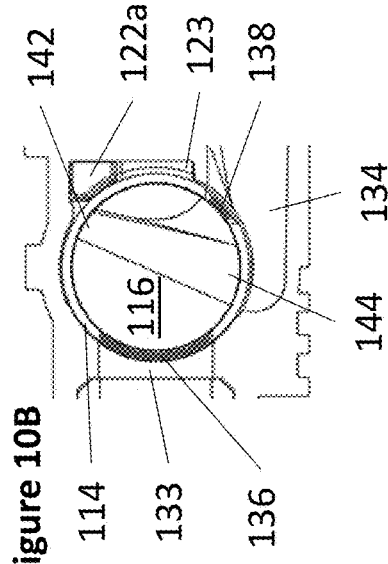
Figure 10A
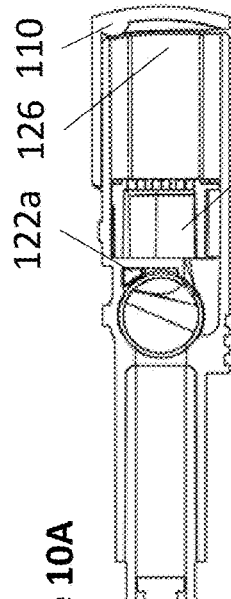
Figure 10B
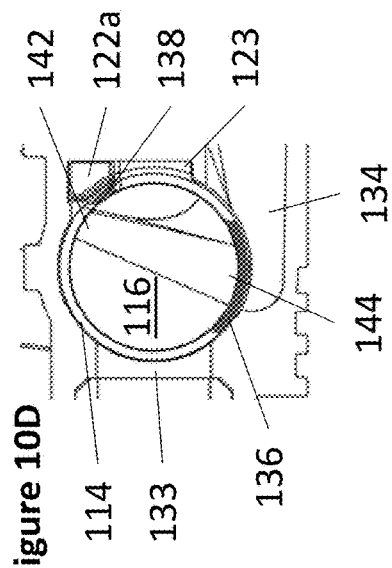
Figure 10C
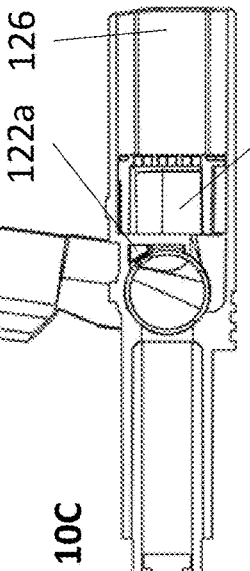
Figure 10D
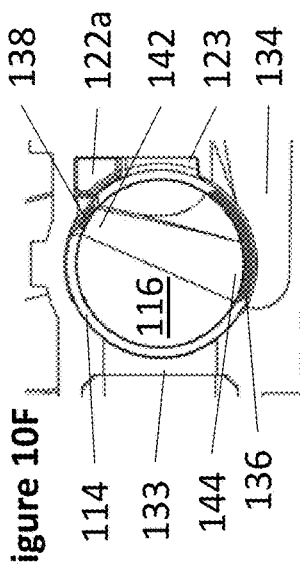
Figure 10E
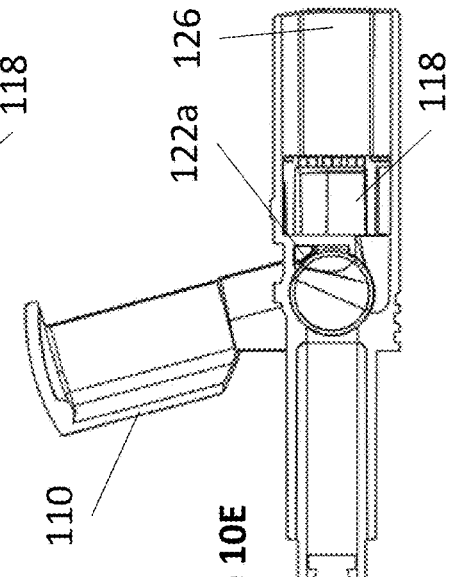
Figure 10F
Figure 10A – Figure 10F

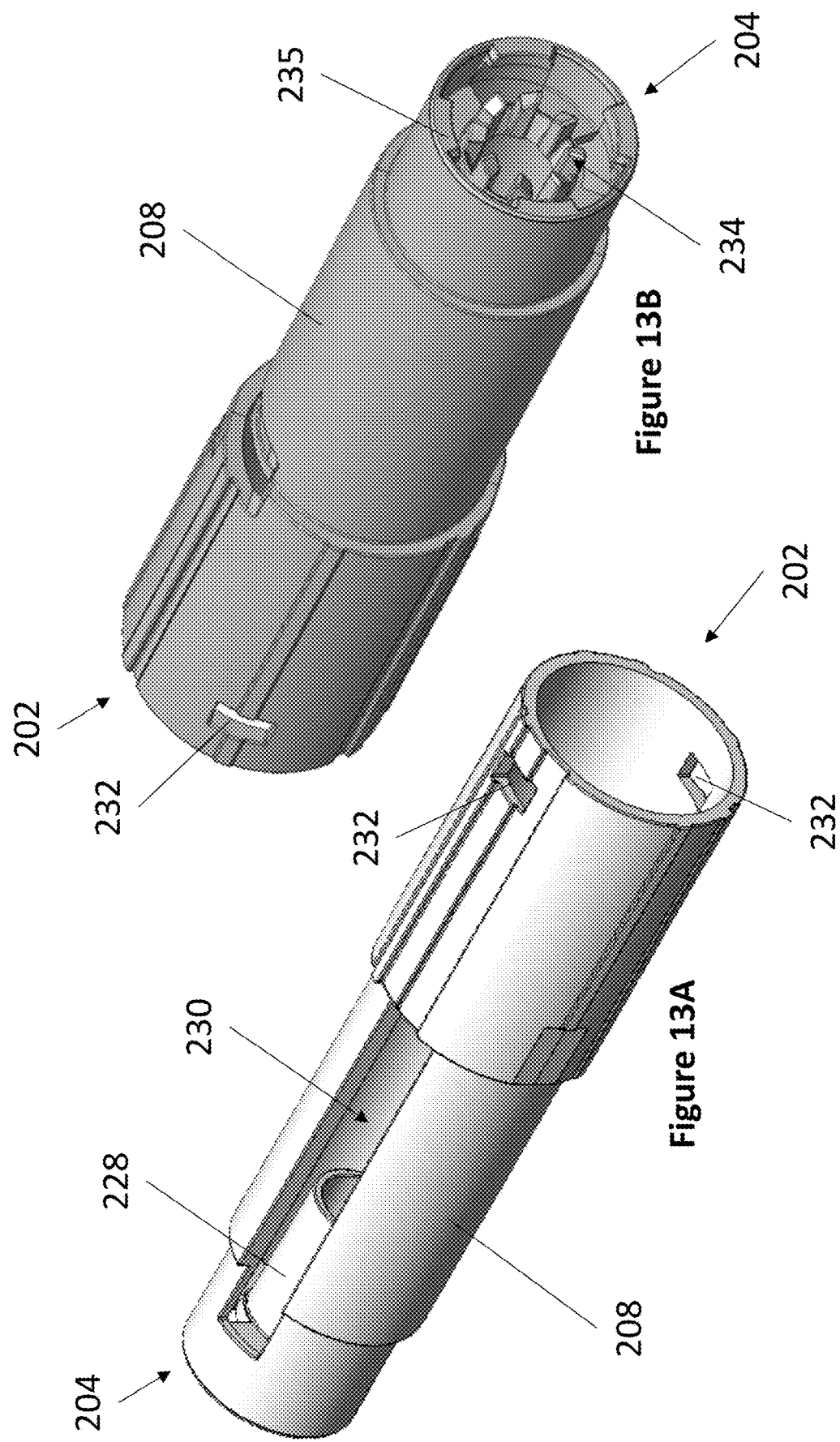

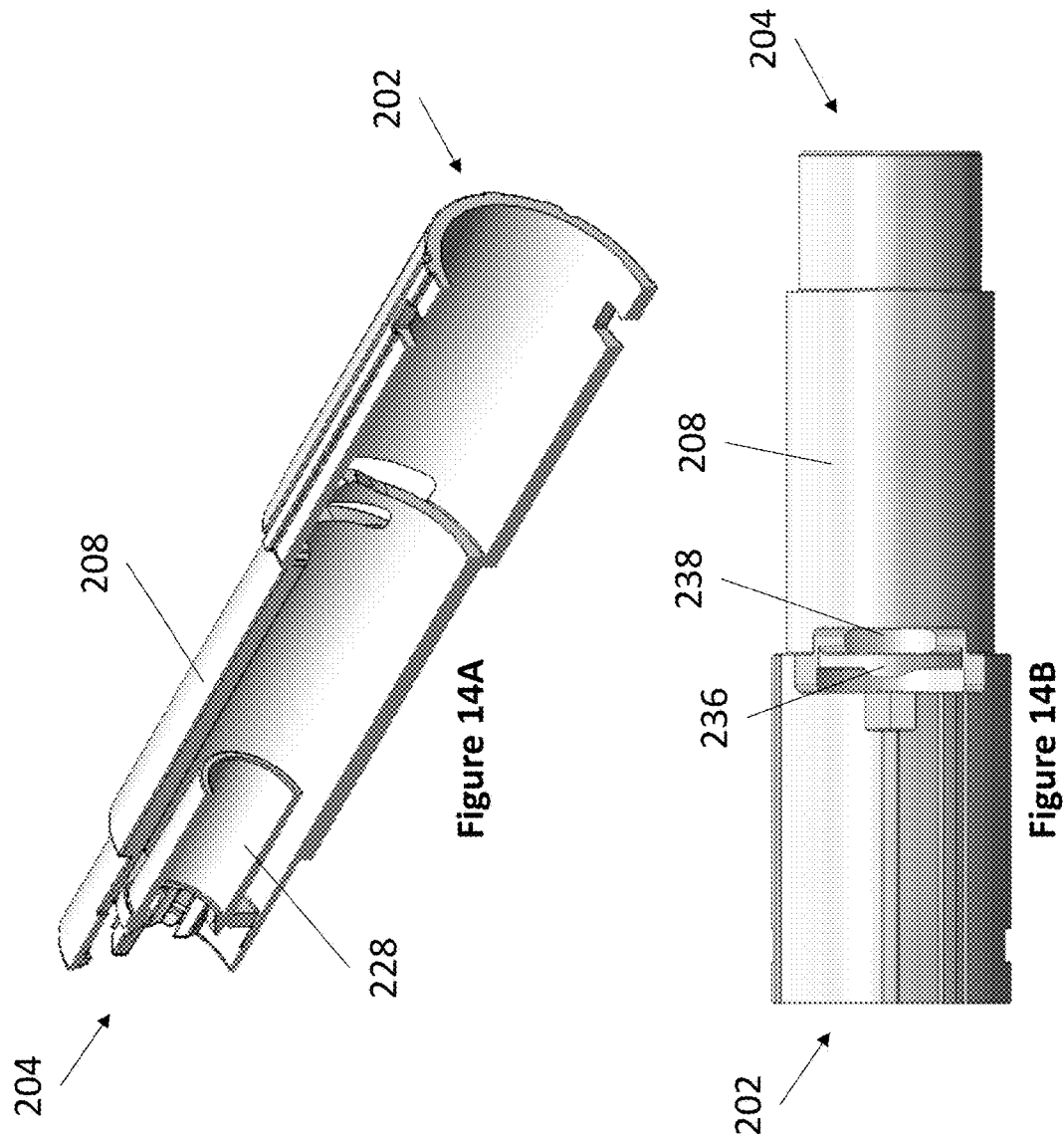

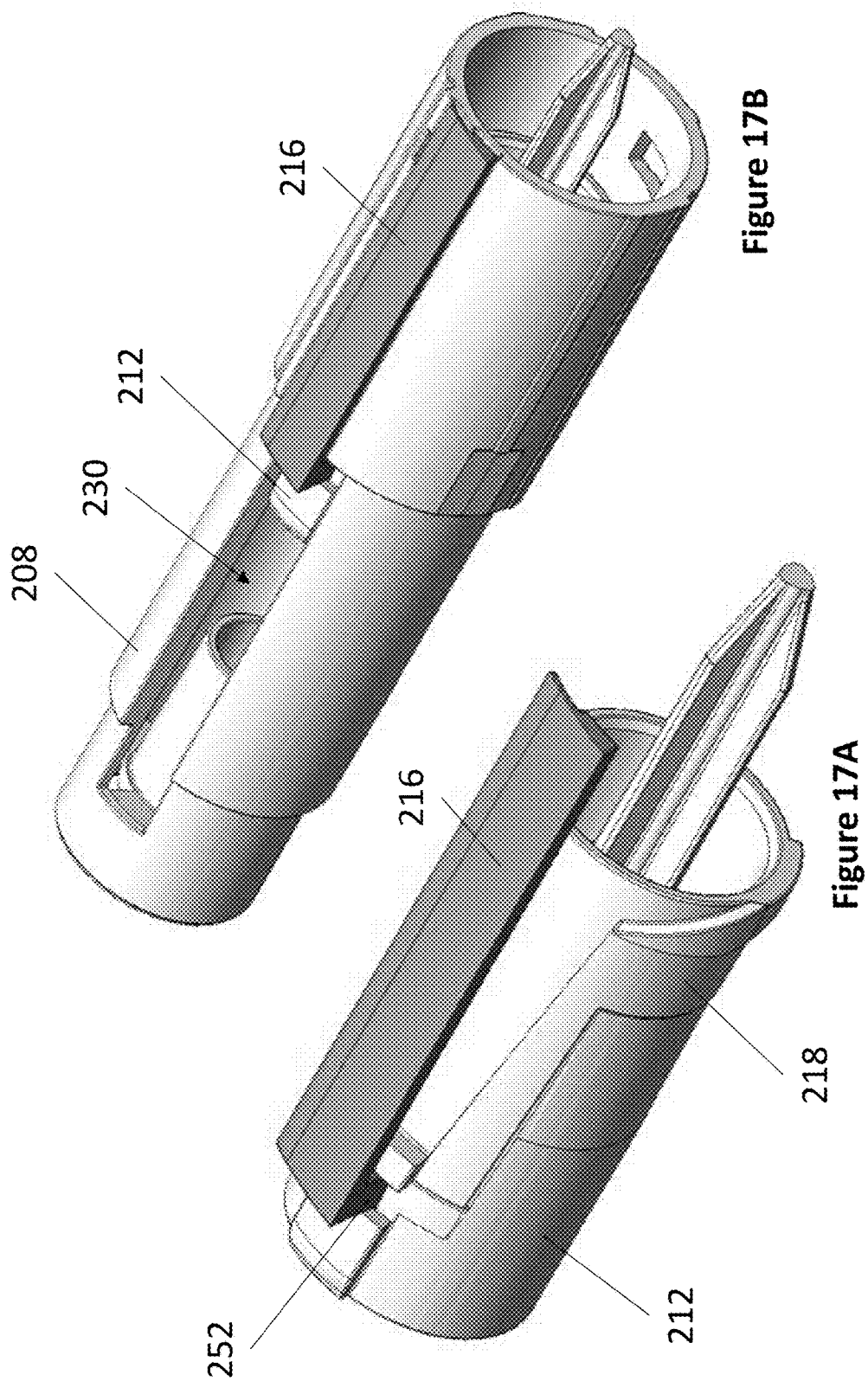

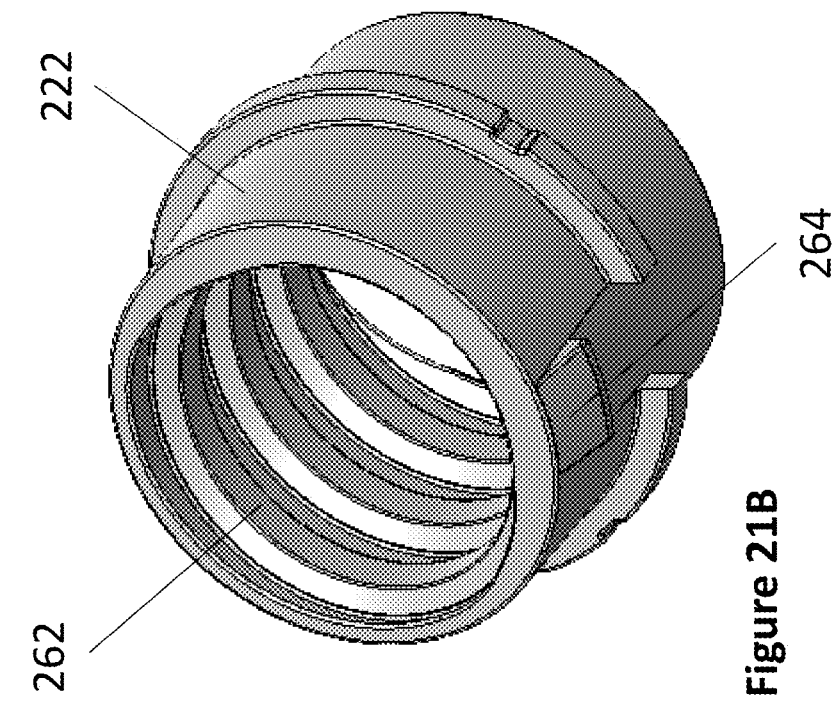
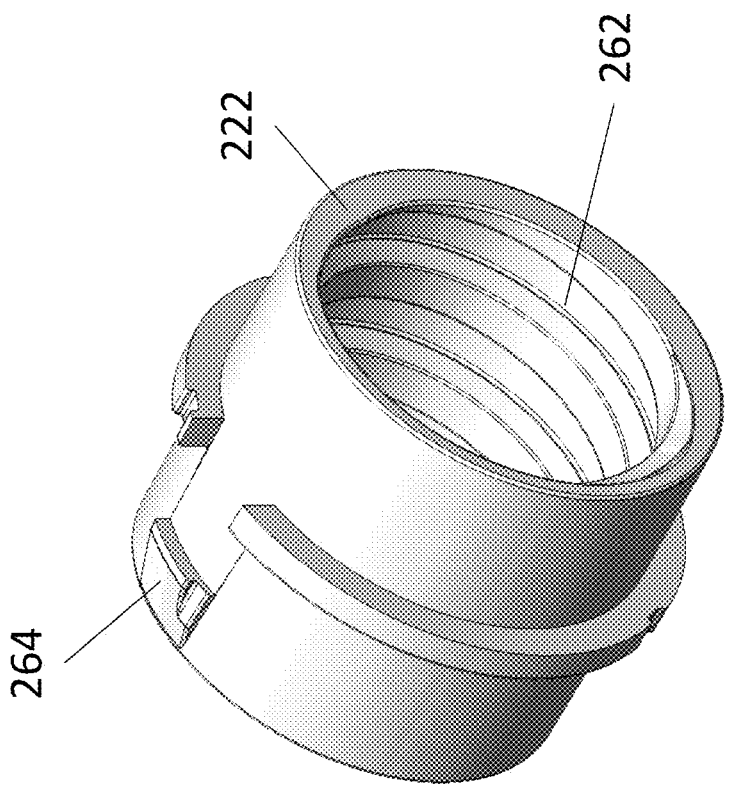
Figure 21A
Figure 21B
Figure 21A – Figure 21B

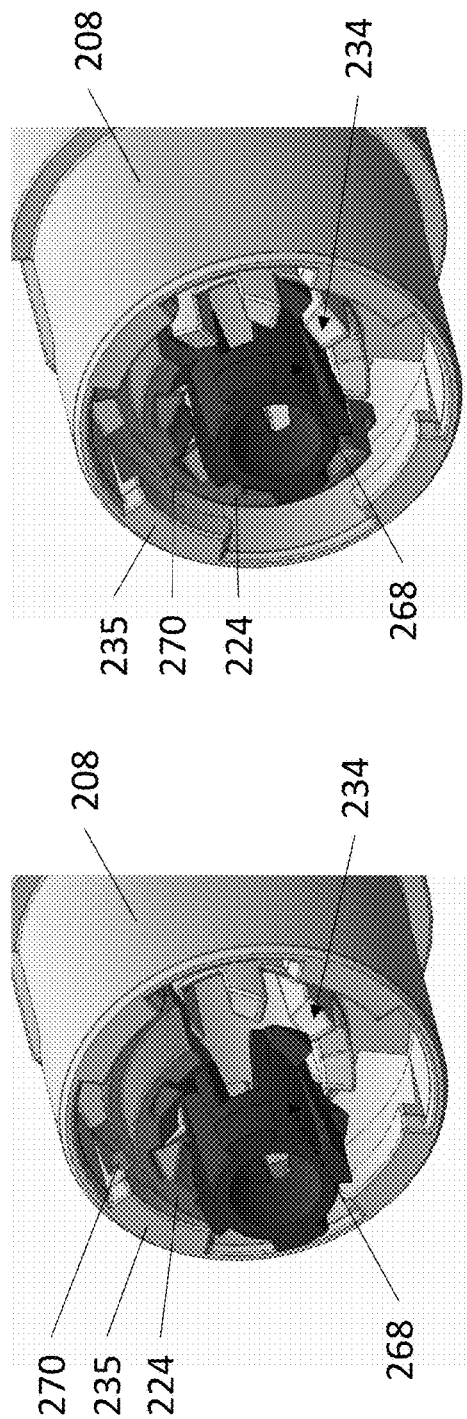
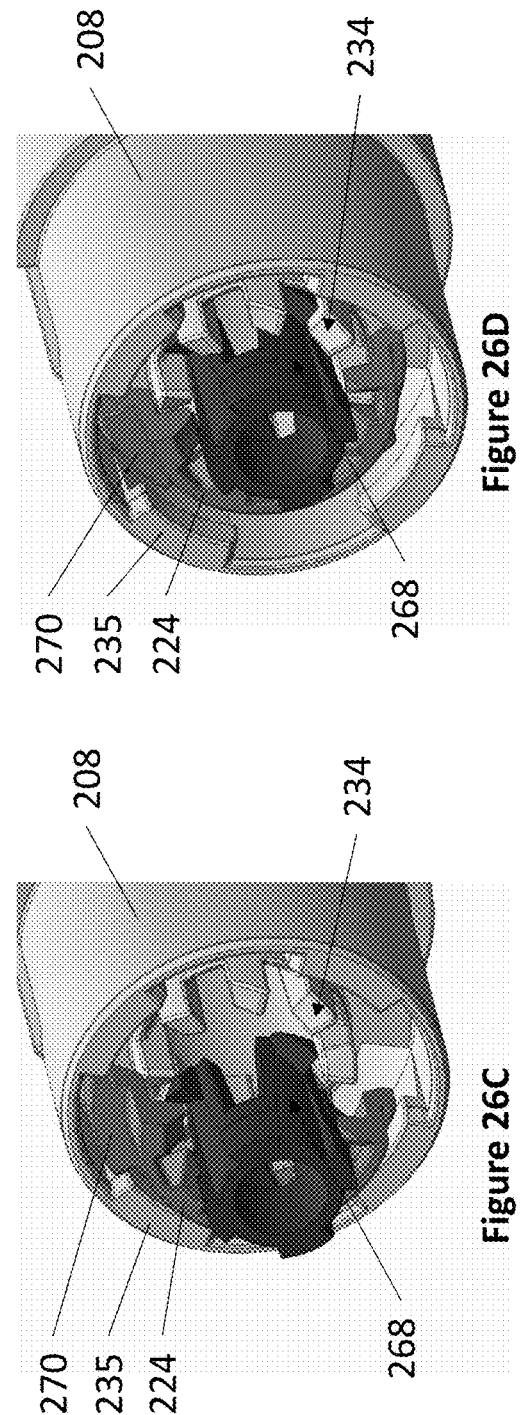
Figure 26A – Figure 26D

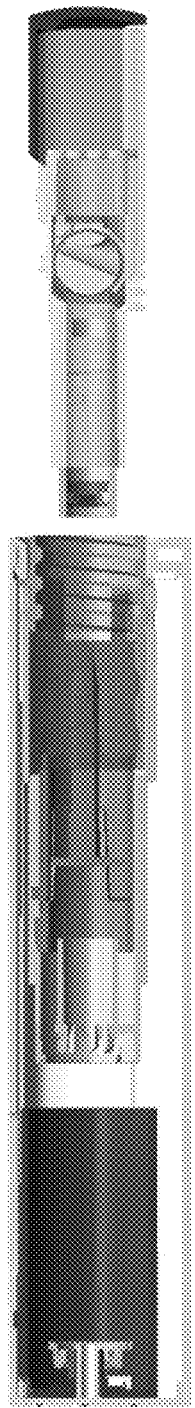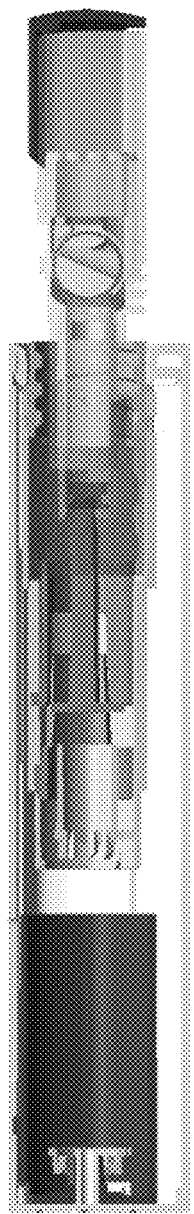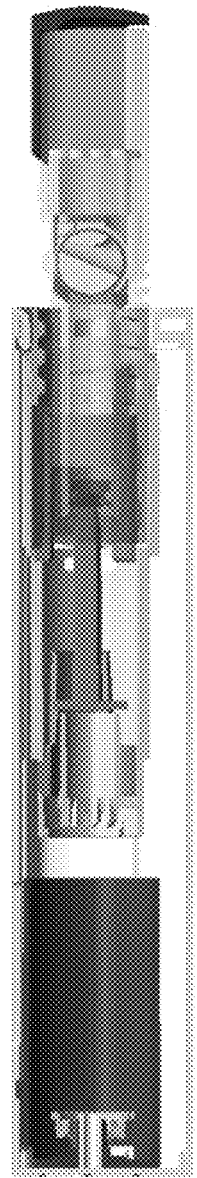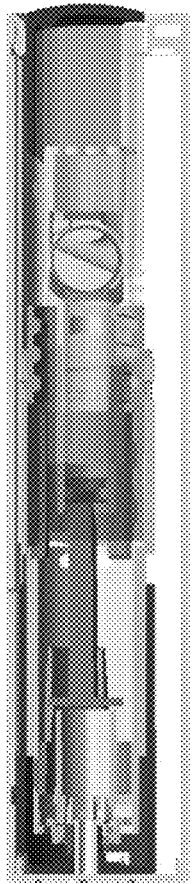
Figure 27A  Figure 27B  Figure 27C  Figure 27D
Figure 27A – Figure 27D

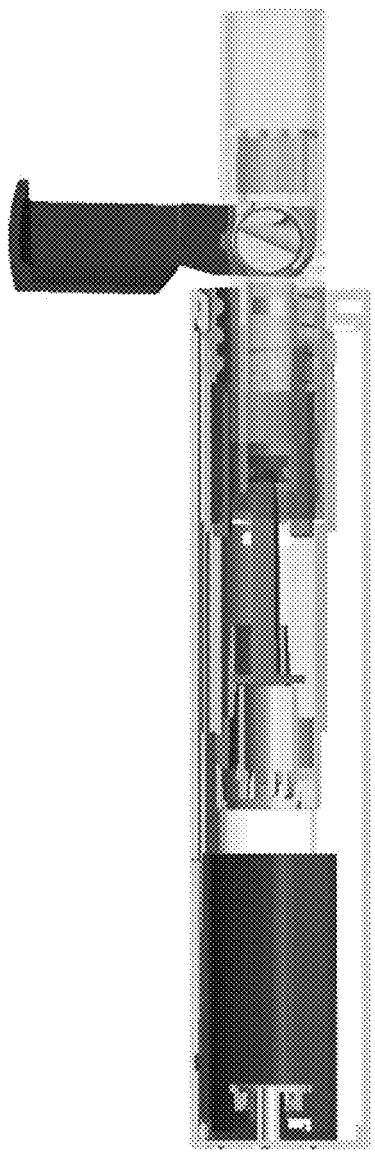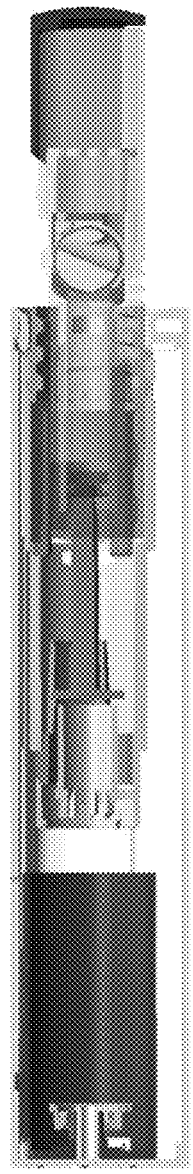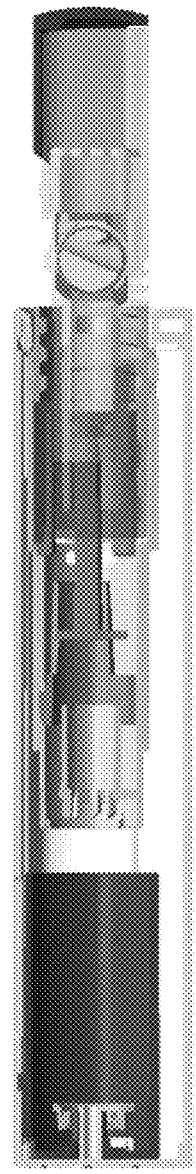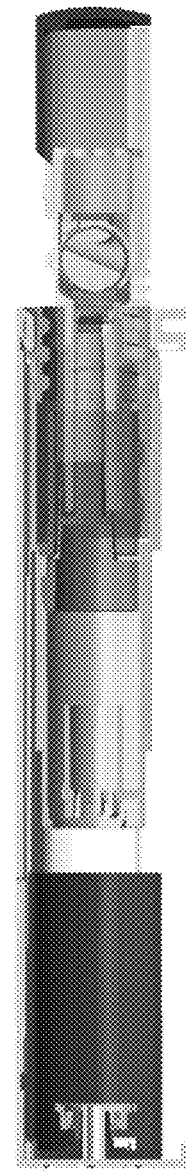
Figure 28A  Figure 28B  Figure 28C  Figure 28D
Figure 28A – Figure 28D

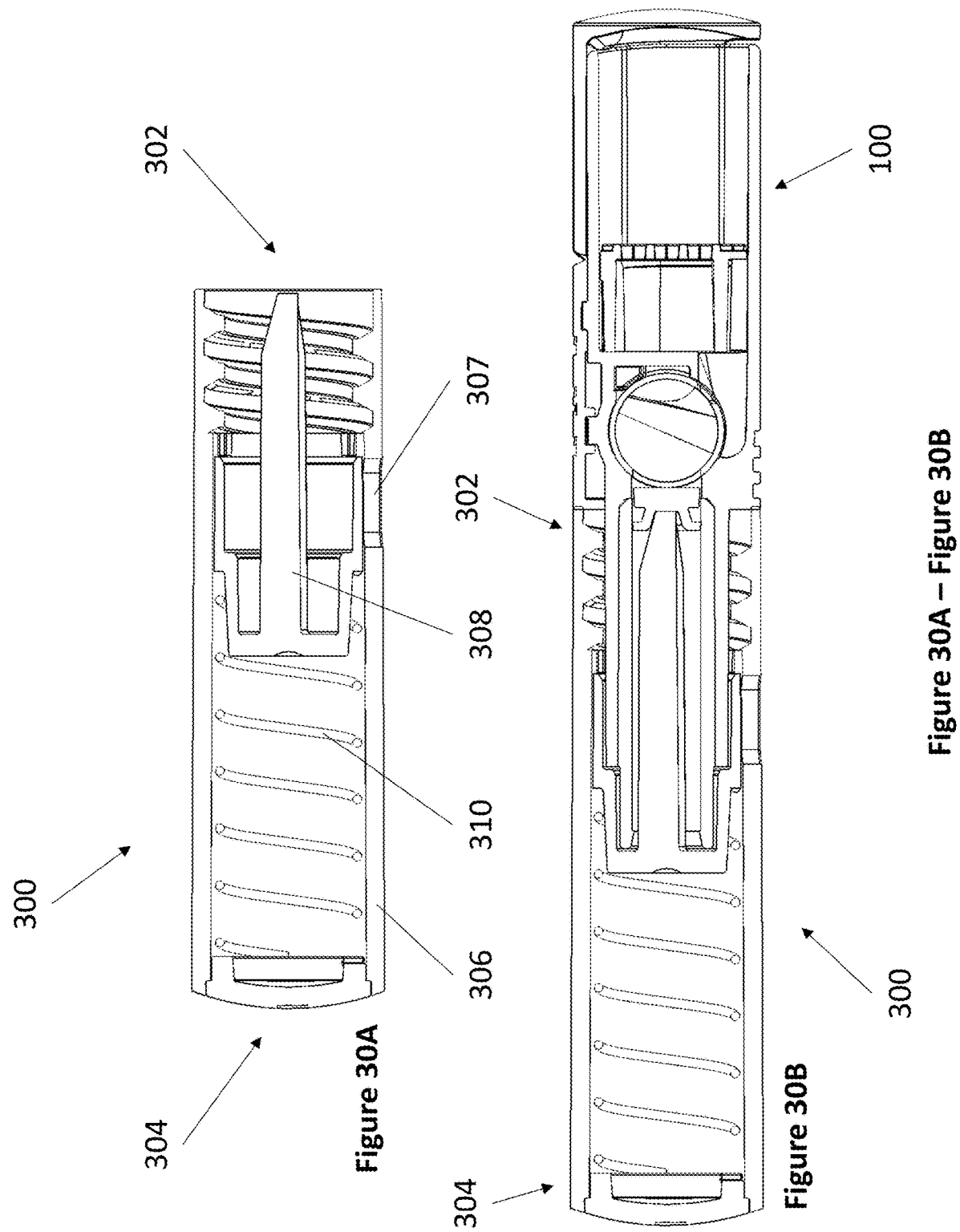

DRY POWDER INHALER

CROSS-REFERENCE TO RELATED APPLICATIONS

This application claims priority to provisional patent application Nos. 62/450,327 filed on Jan. 25, 2017, and 62/365,201 filed on Jul. 21, 2016, both of which are incorporated herein by reference in their entirety.

BACKGROUND OF THE INVENTION

Due to the well documented health hazards of traditional tobacco cigarettes to smokers and bystanders, there has been a shift in the marketplace to find suitable alternatives for the delivery of nicotine to the lungs of a subject. Ideally, nicotine should be delivered to the subject's lungs without the creation of second hand smoke, and without the unpleasant odors associated with traditional tobacco smoking. One mechanism to achieve this is via inhalation of nicotine as a dry powder formulation. In such systems, a dry powder inhaler is used to deposit the powder on the inner surfaces of the lungs for absorption into the bloodstream. Unfortunately though, most dry powder inhalers have numerous undesirable features.

For example, many devices that utilize powder reservoirs have difficulty delivering properly metered doses, advancing the powder through the reservoirs as they are being emptied, and delivering the powder doses adequately to a user. Current powder delivery devices, including the Turbuhaler®, the Twisthaler®, and the NEXThaler, are also limited by ease of use and general design. The above mentioned devices require a user to hold the device upright to ensure proper dose delivery, and have the distinct profiles of prescription medication.

Current powder delivery devise are also incapable of delivering adequate powder doses at flow rates comparable to traditional tobacco smoking. Medical dry powder inhalers require high inspiratory flow rates, typically in the range of 60 liters/min (L/min) to 100 L/min or higher. A flow rate that is too low, such as in the range of 15 L/min or lower, would take too long of a draw for each dose to feel natural. Ideally, the flow rate should be in the range of 30 L/min to emulate traditional tobacco smoking.

One existing device is shown in U.S. Pat. No. 6,234,169 to Bulbrook ("Bulbrook"), which describes a cone shaped device that protrudes into a dry powder storage reservoir to generate a vortex-like effect inside the cone. The device uses the vortex to dip down inside the storage reservoir and pick up a slug of powder and deliver it to the airways of an individual. However, a significant limitation of the Bulbrook design is that it does not provide adequate energy inside the storage reservoir to deagglomerate the powder sufficiently to deliver the desired aerosol to the user. The Bulbrook design also lacks a reliable method of preventing accidental powder release or a feature for switching storage reservoirs.

Thus, there is a need in the art for a reservoir dry powder inhaler that can reliably meter a dry powder formulation independent of orientation and deliver a suitably deagglomerated dry powder for inhalation while maintaining ease of use in a discrete design. The present invention satisfies this need.

SUMMARY OF THE INVENTION

In one aspect, the present invention relates to a dry powder cartridge device comprising: an elongate body having an anterior end and a posterior end; a delivery lumen positioned at the anterior end of the body; a powder reservoir positioned at the posterior end of the body; a powder metering drum assembly positioned anterior to the powder reservoir; and an actuating cap positioned at the anterior end of the body mechanically engaged to the powder metering drum; wherein an amount of powder within the powder reservoir is advanced towards the powder metering drum by a piston.

In one embodiment, the elongate body comprises at least one air inlet fluidly connected to the powder metering drum assembly. In one embodiment, the delivery lumen comprises a side air inlet to introduce a vortex airflow into the delivery lumen. In one embodiment, the delivery lumen comprises a mesh to break apart powder agglomerates and vortex airflow. In one embodiment, a flow of air introduced through the delivery lumen at a rate of 20 to 40 L/min is sufficient to break apart powder agglomerates and vortex airflow.

In one embodiment, the powder metering drum assembly comprises a cylindrical outer drum and a cylindrical inner drum insert having a curved exterior, wherein the cylindrical outer drum lies flush against and is rotatable along the curved exterior of the inner drum insert, and wherein the cylindrical outer drum comprises a powder dose aperture and an air aperture positioned opposite from the powder dose aperture. In one embodiment, the inner drum insert has a delivery air inlet on the curved exterior facing upwards, a delivery air outlet on the curved exterior facing downwards opposite from the delivery air inlet, and a lumen passing through the inner drum insert connecting the delivery air inlet and the delivery air outlet.

In one embodiment, the actuating cap rotates the outer drum about the curved exterior of the inner drum insert. In one embodiment, rotating the outer drum to face the powder dose aperture towards the powder reservoir deposits a dose of dry powder from the powder reservoir into a space bordered by the powder dose aperture and the curved exterior of the inner drum insert. In one embodiment, rotating the outer drum to align the powder dose aperture with the delivery air outlet simultaneously aligns the air aperture with the delivery air inlet. In one embodiment, the air aperture does not begin to overlap with the delivery air inlet until the powder dose aperture completely disengages from the powder reservoir. In one embodiment, the alignment of the powder dose aperture with the delivery air outlet and the air aperture with the delivery air inlet creates a fluid communication between the at least one air inlet of the elongate body, the lumen of the inner drum insert, and the delivery lumen.

In another aspect, the present invention relates to a dry powder inhaler casing device, comprising: a casing having a lumen throughout, an open anterior end, and a closed posterior end; a plunger within the casing lumen; and a plunger spring within the casing lumen positioned between the plunger and the closed posterior end of the casing; wherein the open anterior end of the casing is sized to accept the cartridge of the present invention.

In one embodiment, the plunger spring presses the plunger against the piston of the cartridge, such that the piston is advanced in an anterior direction as the powder reservoir is depleted. In one embodiment, the casing comprises a window through which a portion of the plunger is visible, such that the advancement and position of the plunger can be determined through the window.

In another aspect, the present invention relates to a dry powder inhalation system, comprising: a dry powder inhaler casing device; at least one cartridge having a powder reservoir and a powder metering drum assembly; and at least one amount of powder.

In one embodiment, the at least one amount of powder is preloaded into the at least one cartridge powder reservoir. In one embodiment, the at least one amount of powder is manually loaded into the at least one cartridge powder reservoir. In one embodiment, the at least one powder inhaler casing and the at least one cartridge are interchangeable. In one embodiment, the at least one cartridge is disposable.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A through FIG. 1B depict perspective views of an exemplary dry powder inhaler (DPI) cartridge from the front left (FIG. 1A) and from the rear right (FIG. 1B).

FIG. 3A through FIG. 3D depict perspective views of an exemplary DPI cartridge body from the front left (FIG. 3A), from the rear right (FIG. 3B), side cross sectional view from the front left (FIG. 3C), and top cross sectional view from the front left (FIG. 3D).

FIG. 8A and FIG. 8B depict perspective views of an exemplary DPI cartridge reservoir from the front left (FIG. 8A) and cross sectional view from the front left with piston visible (FIG. 8B).

FIG. 9A through FIG. 9C depict various views of an exemplary DPI cartridge cyclone insert from the front left (FIG. 9A), from the rear right (FIG. 9B), and from the rear (FIG. 9C).

FIG. 10A through FIG. 10F depict wireframe cross sectional views of an exemplary DPI cartridge during various stages of actuation. FIG. 10A and FIG. 10B depict the cap closed and the corresponding drum orientation. FIG. 10C and FIG. 10D depict the cap open part way and the corresponding drum orientation. FIG. 10E and FIG. 10F depict the cap open completely and the corresponding drum orientation.

FIG. 13A and FIG. 13B depict perspective views of an exemplary triangular DPI shuttle part from the front left (FIG. 13A) and from the rear right (13B).

FIG. 14A and FIG. 14B depict various views of an exemplary triangular DPI shuttle part from the front left cross sectional view (FIG. 14A) and from the right (FIG. 14B).

FIG. 17A and FIG. 17B depict front left perspective views of an exemplary triangular DPI fuel gauge part combined with a plunger part and enforcer part (FIG. 17A) and combined with a shuttle part (FIG. 17B).

FIG. 21A and FIG. 21B depict a front left perspective view (FIG. 21A) of an exemplary triangular DPI shuttle cap part.

FIG. 26A through FIG. 26D depict cutaway views of the actuation mechanism between an exemplary triangular DPI chassis part, rotary lock part, and shuttle part in sequence.

FIG. 27A through FIG. 27D depict cross sectional left side views of an exemplary DPI cartridge being loaded into an exemplary triangular DPI in sequence.

FIG. 28A through FIG. 28D depict cross sectional left side views of an exemplary DPI cartridge dispensing a dose of a dry powder and advancing the reservoir supply of dry powder while loaded in an exemplary triangular DPI in sequence. FIG. 28A and FIG. 28B depict the advancement of the reservoir supply after dispensing a single dose of dry powder. FIG. 28C depicts the advancement of the reservoir supply after dispensing several doses of dry powder. FIG. 28D depicts a depleted reservoir supply after dispensing all doses of dry powder.

FIG. 30A and FIG. 30B depict cross sectional left side views of an exemplary micro DPI without a DPI cartridge (FIG. 30A) and with a DPI cartridge (FIG. 30B).

DETAILED DESCRIPTION

Figure 2:
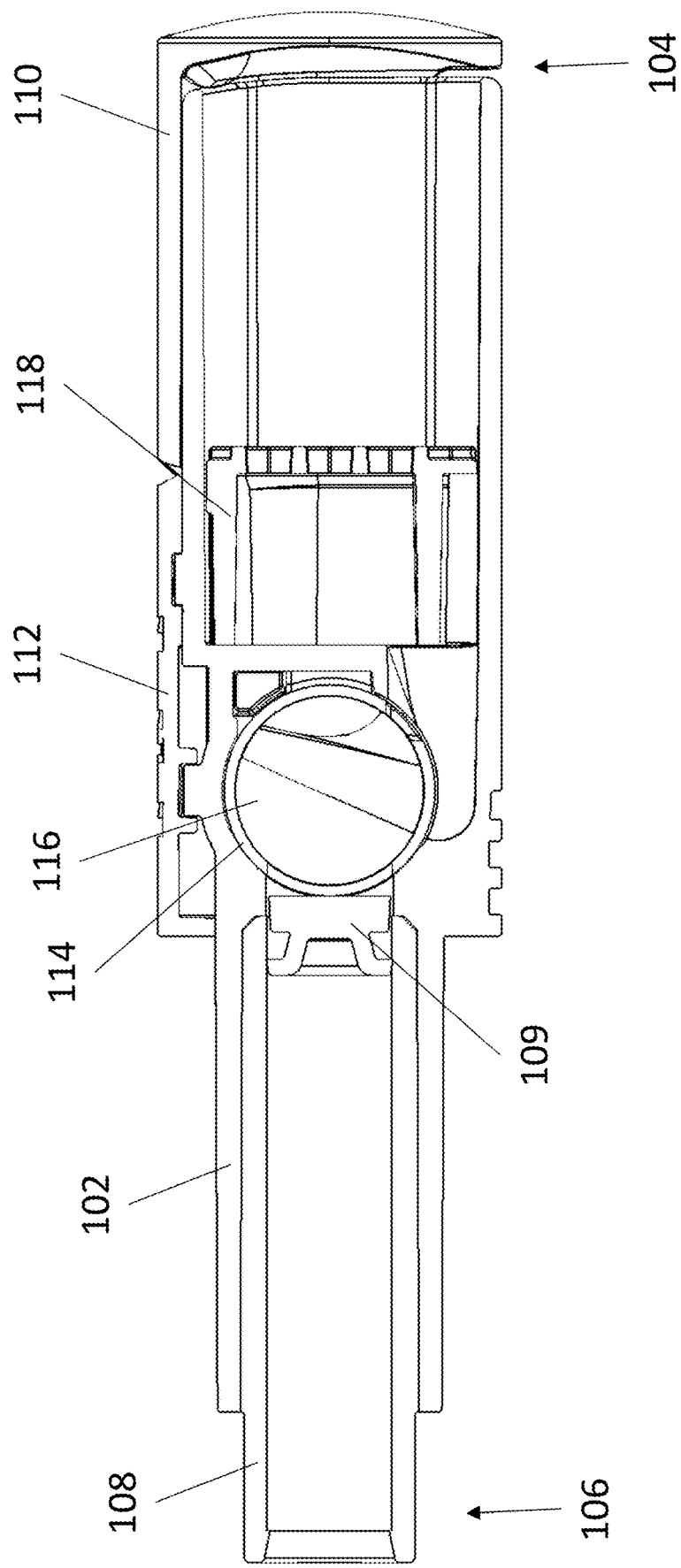
FIG. 2 depicts a wireframe cross sectional view of an exemplary DPI cartridge from the left.
Figure 4A:
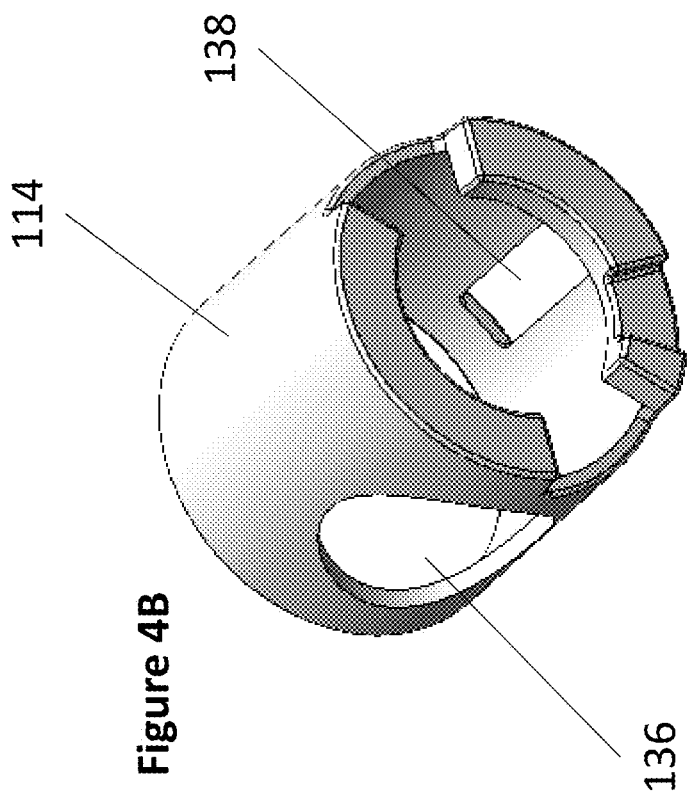
FIG. 4A and FIG. 4B depict perspective views of an exemplary DPI cartridge drum from the front left (FIG. 4A) and from the rear left (FIG. 4B).
Figure 4B:
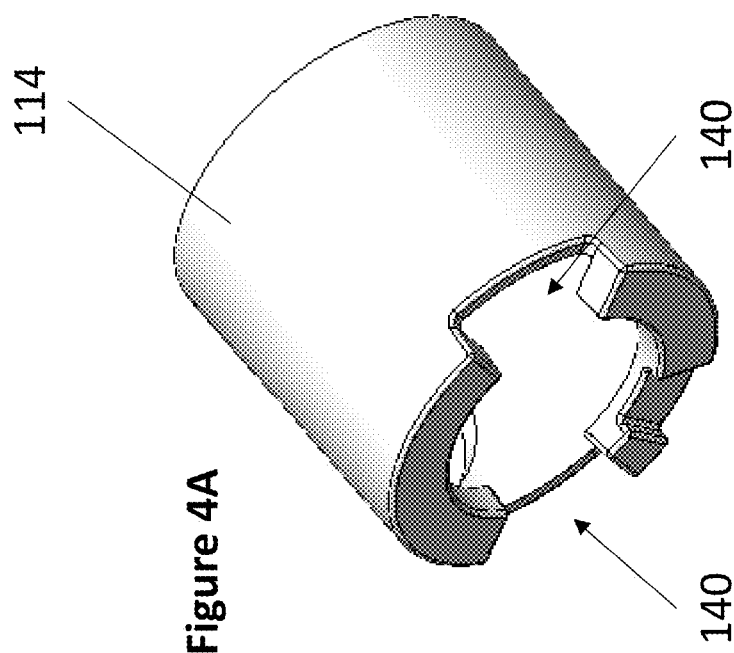
Figure 5A:
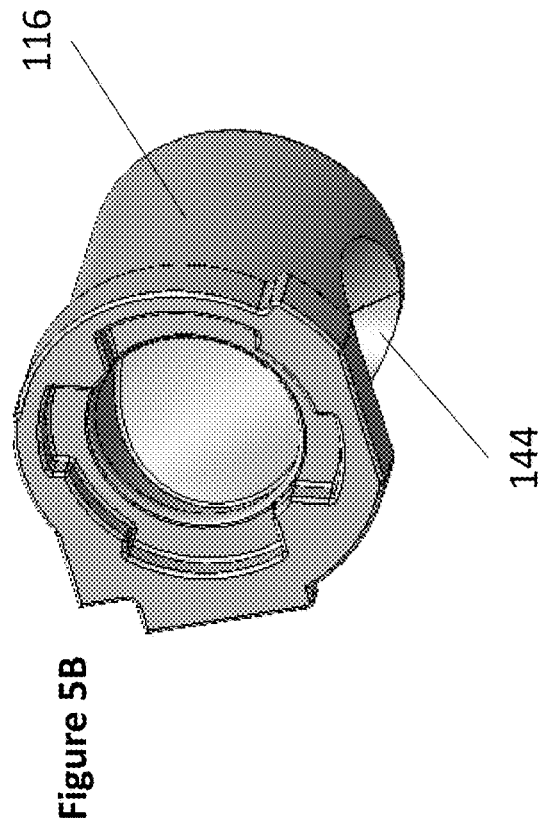
FIG. 5A and FIG. 5B depict perspective views of an exemplary DPI cartridge drum insert from the front left (FIG. 5A), from the rear right (FIG. 5B), and from the bottom (FIG. 5C).
Figure 5B:
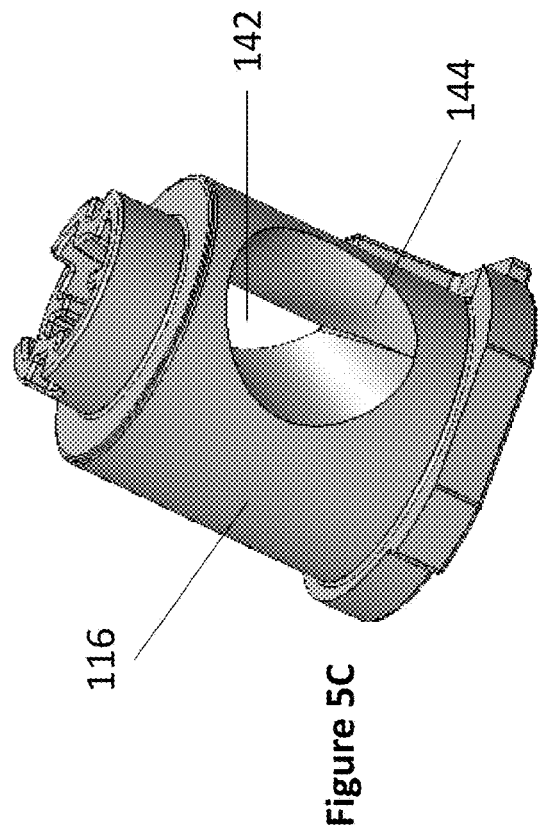
Figure 5C:
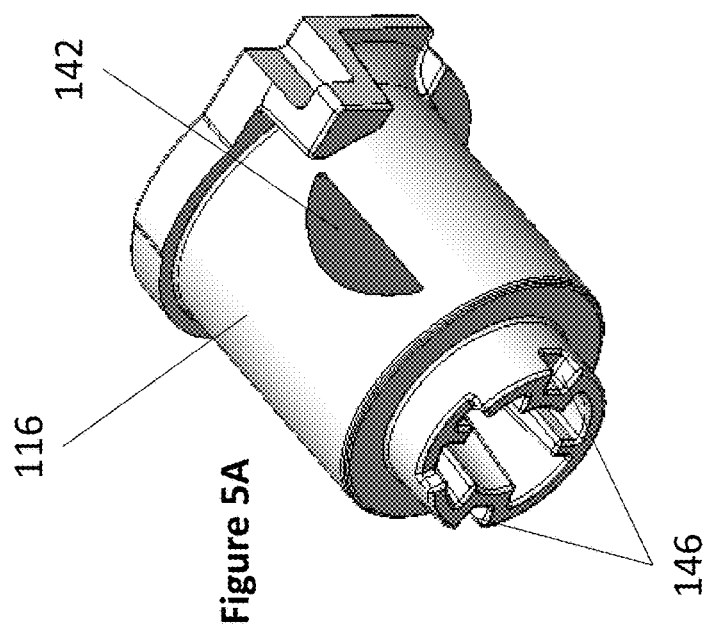
Figure 6A:
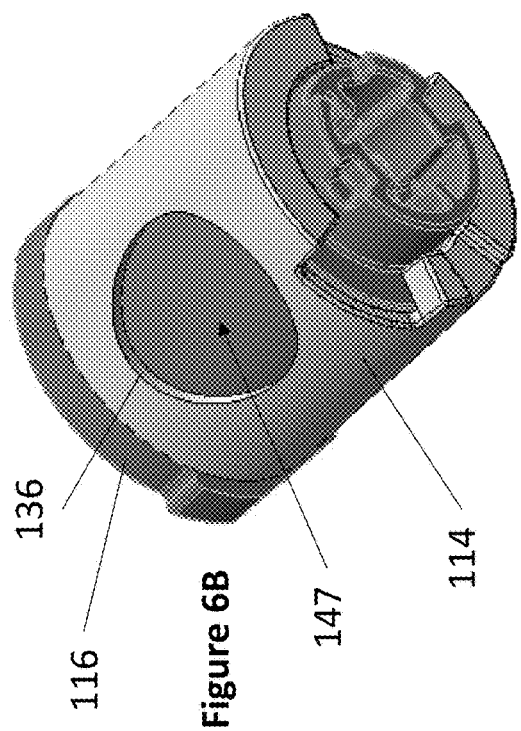
FIG. 6A through FIG. 6C depict perspective views of an exemplary DPI cartridge drum insert (shaded) within an exemplary DPI cartridge drum from the front left (FIG. 6A), from the rear left (FIG. 6B), and from the bottom (FIG. 6C).
Figure 6B:
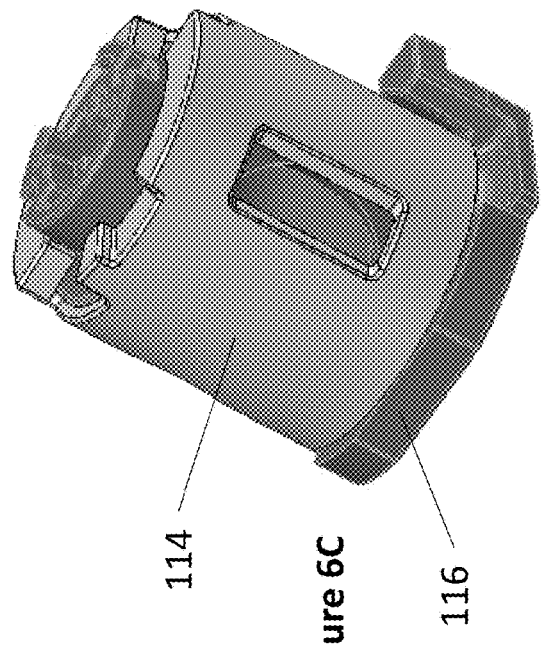
Figure 6C:
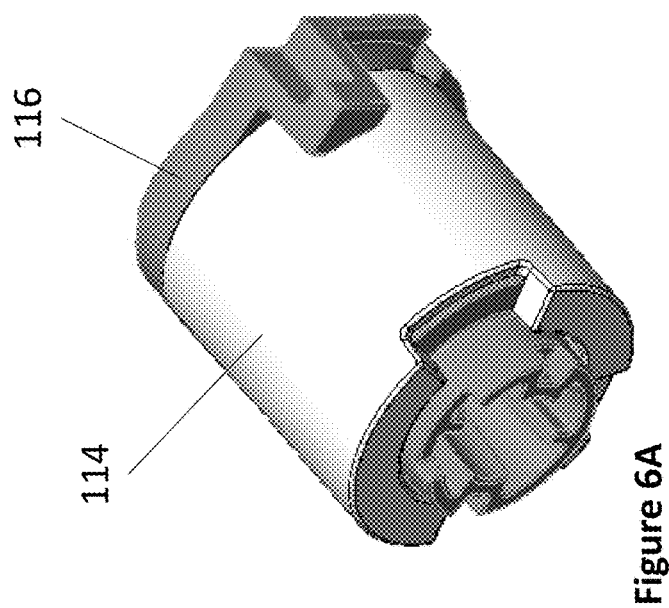
Figure 7:
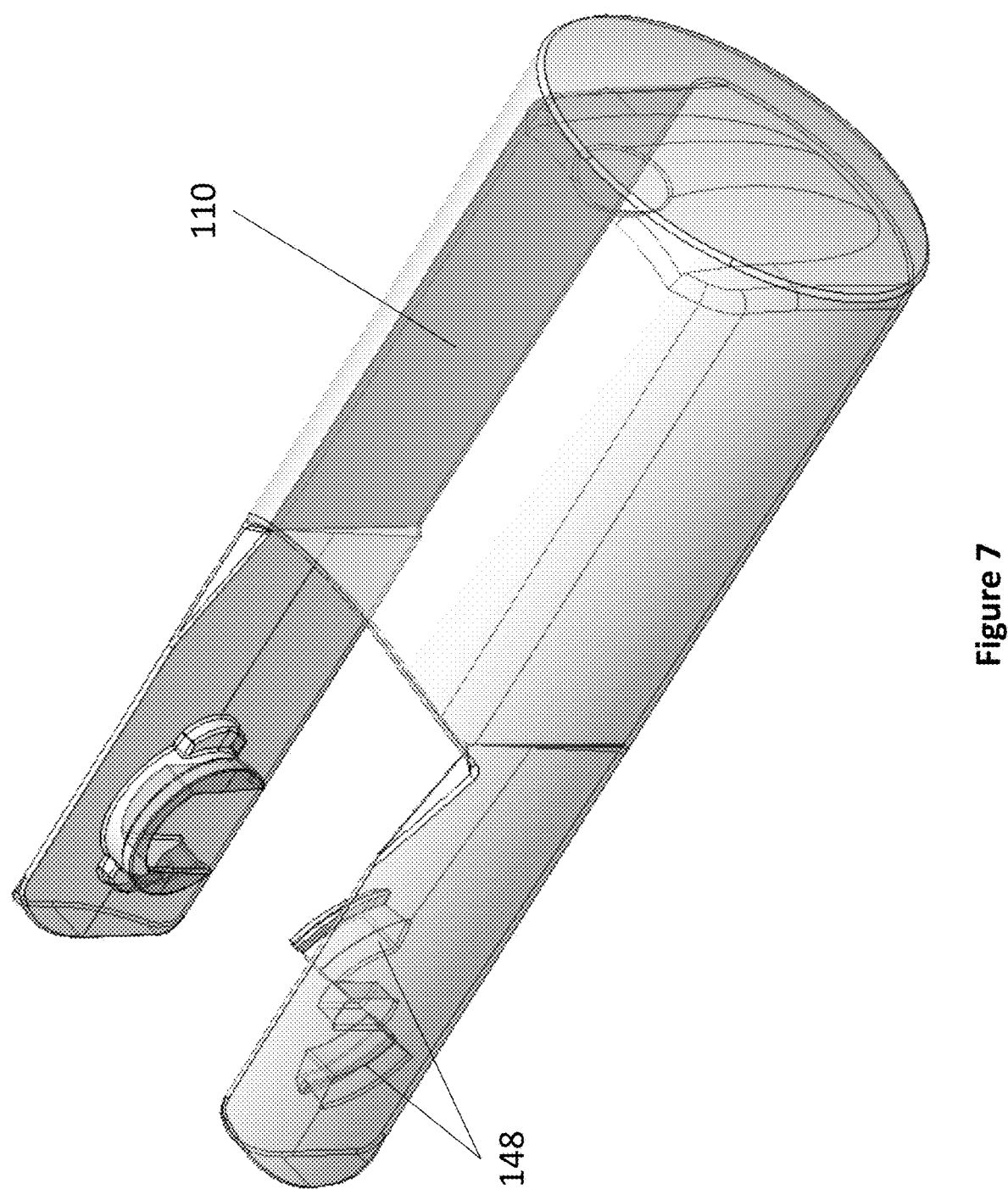
FIG. 7 depicts a perspective view of an exemplary DPI cartridge cap from the front left.

The present invention provides in part dry powder inhaler (DPI) devices for dispensing dry powder and methods for using the same. The DPI devices feature exchangeable cartridges having drum mechanisms that prepare metered doses of dry powder, and are able to direct air in a turbulent manner sufficient to entrain and deagglomerate a dose of dry powder for delivery into a user's lungs. The DPI devices feature a reservoir of dry powder advanced by a plunger, as well as a gauge that advances with the plunger to indicate the amount of dry powder remaining in the reservoir.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Dry Powder Inhaler Cartridge

In one aspect, the present invention provides dry powder inhaler (DPI) cartridges comprising dry powder storage and delivery features. The DPI cartridges may be used with any compatible DPI with little or no variation in design.

Referring now to FIG. 1A and FIG. 1B, an exemplary DPI cartridge 100 is depicted. Cartridge 100 has an anterior end 104 and a posterior end 106 and comprises cartridge body 102, cap 110 at anterior end 104, and reservoir 108 at posterior end 106. In certain embodiments, cartridge 100 comprises trim 112. Trim 112 can be ornamental, such as displaying a logo, or informative, such as being color-coded or labeled to indicate dry powder formulation.

Referring now to FIG. 2, the components of an exemplary DPI cartridge 100 are depicted. Cartridge 100 further comprises drum 114, drum insert 116, and cyclone insert 118. Reservoir 108 further comprises piston 109.

Referring now to FIG. 3A through FIG. 3D, cartridge body 102 is now described. Beginning at posterior end 106, cartridge body 102 comprises reservoir port 124, threads 120, air inlet 122*a*, air inlet 122*b*, air inlet 122*c*, air channel 123, and delivery lumen 126. Reservoir slots 121 are provided for securing reservoir 108, as described elsewhere herein. Trim tabs 132 are provided for attaching trim 112. Drum assembly port 128 is provided to accept drum 114 and drum insert 116. Drum insert tabs 130 secure drum insert 116 in place, as described elsewhere herein. Air inlet 122*b* and 122*c* perform the additional function of securing cyclone insert 118, as described elsewhere herein. The cross sectional views of cartridge body 102 reveal powder entry port 133 and powder delivery chamber 134.

Referring now to FIG. 4A and FIG. 4B, drum 114 is now described. Drum 114 comprises a substantially hollow cylindrical shape having open ends, wherein a curved surface has a powder dose aperture 136 and air aperture 138. On the left side of drum 114, actuation slots 140 are provided to engage cap 110, as described elsewhere herein.

Referring now to FIG. 5A through FIG. 5C, drum insert 116 is now described. Drum insert 116 comprises a substantially solid cylindrical shape having closed ends, wherein a curved outer surface has delivery air inlet 142 and delivery air outlet 144 forming the two ends of a lumen passing through the width of drum insert 116. Due to various spring loads acting upon the inner components of device 10, drum insert 116 must be accurately and securely positioned within drum assembly port 128 of cartridge body 102 to maintain the specific clearances necessary for powder containment and consistent airflow. Drum insert 116 is therefore provided with structural stabilizing features such as drum insert slots 146 that engage with drum insert tabs 130 to securely position drum insert 116, enabling smooth actuation of drum 114 about drum insert 116.

Referring now to FIG. 6A through FIG. 6C, the combination of drum 114 and drum insert 116 is now described. Drum 114 fits flush over drum insert 116 such that powder dose aperture 136 forms powder dose pocket 147 against the outer surface of drum insert 116. Drum 114 is rotatable about the outer surface of drum insert 116, wherein an amount of dry powder contained in powder dose pocket 147 may be relocated about the outer surface of drum insert. In various configurations, drum 114 can be rotated to align powder dose aperture 136 with delivery air outlet 144 and air aperture 138 with delivery air inlet 142, as described elsewhere herein.

Referring now to FIG. 7, cap 110 is now described. Cap 110 comprises actuation tabs 148 to engage actuation slots 140, such that cap 110 may be actuated to rotate drum 114 about drum insert 116, as described elsewhere herein. Cap 110 is shaped to cover delivery lumen 126 when secured onto cartridge body 102, as depicted in FIG. 1A and FIG. 1B.

Referring now to FIG. 8A and FIG. 8B, reservoir 108 is now described. Reservoir 108 comprises a substantially hollow cylindrical shape having open ends, wherein powder lumen 150 is disposed within reservoir 108 to hold an amount of dry powder. Piston 109 is positioned posterior to the amount of dry powder to compact and advance the amount of dry powder within reservoir 108. FIG. 8B depicts piston 109 in an anterior position, indicating that reservoir 108 is empty. While not pictured, a full or partially filled reservoir 108 may further comprise a stopper or seal at anterior end 104 to secure an amount of dry powder within reservoir 108. Reservoir 108 comprises reservoir tabs 151 to engage reservoir slots 121 to secure reservoir 108 within cartridge body 102.

Referring now to FIG. 9A through FIG. 9C, cyclone insert 118 is now described. Cyclone insert 118 comprises cyclone mesh 154 and cyclone air inlet 156. Cyclone air inlet 156 introduces lateral air 158 from air inlet 122b to generate a vortex within cyclone insert 118. Cyclone mesh 154 is provided to break apart dry powder agglomerates during dry powder delivery and to disrupt the vortex.

Referring now to FIG. 10A through FIG. 10F, the mechanism of metering and delivering a dose of dry powder using cartridge 100 is now described. FIG. 10A depicts cap 110 in a closed configuration, with FIG. 10B depicting the corresponding drum 114 orientation. Powder dose aperture 136 (shaded) faces powder entry port 133 to accept an incoming dose of dry powder. FIG. 10C depicts cap 110 in a partially opened configuration, with FIG. 10D depicting the corresponding drum 114 orientation. The actuation of cap 110 has rotated drum 114 such that powder dose aperture 136 (shaded) shears away a dose of dry powder and rotates to overlap delivery air outlet 144 and face powder delivery chamber 134. Overlapping the open space of delivery air outlet 144 aligns the dose of dry powder in powder dose aperture 136 (shaded) with powder delivery chamber 134. FIG. 10E depicts cap 110 in a fully opened configuration, with FIG. 10F depicting the corresponding drum 114 orientation. The full actuation of cap 110 has rotated drum 114 such that powder dose aperture 136 (shaded) aligns with delivery air outlet 144 and air aperture 138 (shaded) aligns with delivery air inlet 142. It should be noted that air aperture 138 does not align with delivery air inlet 142, and therefore no passage of air is allowed, until powder dose aperture 136 full disengages from powder entry port 133 to prevent the inadvertent introduction of excess powder to a dry powder dose. Applying a vacuum to delivery lumen 126 allows air to enter through air inlet 122a, air inlet 122c, and air channel 123, pass through air aperture 138 (shaded), delivery air inlet 142, delivery air outlet 144, powder dose aperture 136, and into powder delivery chamber 134, whereupon the air entrains the dose of dry powder. The air entrained with dry powder then enters the posterior end of cyclone air inlet 156, wherein lateral air 158 sweeps the air entrained with dry powder into a vortex, passes through cyclone mesh 154, and exits through delivery lumen 126. The dimensions and arrangement of the components of cartridge 100 dispense a sufficiently deagglomerated dose of powder using a smooth flow rate of air, such as in the range between 20 and 40 L/min.

Dry Powder Inhalers

In one aspect, the present invention provides dry powder inhalers (DPI) compatible with the DPI cartridges of the present invention. The DPI generally comprise a plunger system that engages the piston of a DPI cartridge to advance an amount of dry powder within the DPI cartridge as the amount of dry powder is diminished with use.

Figure 11:
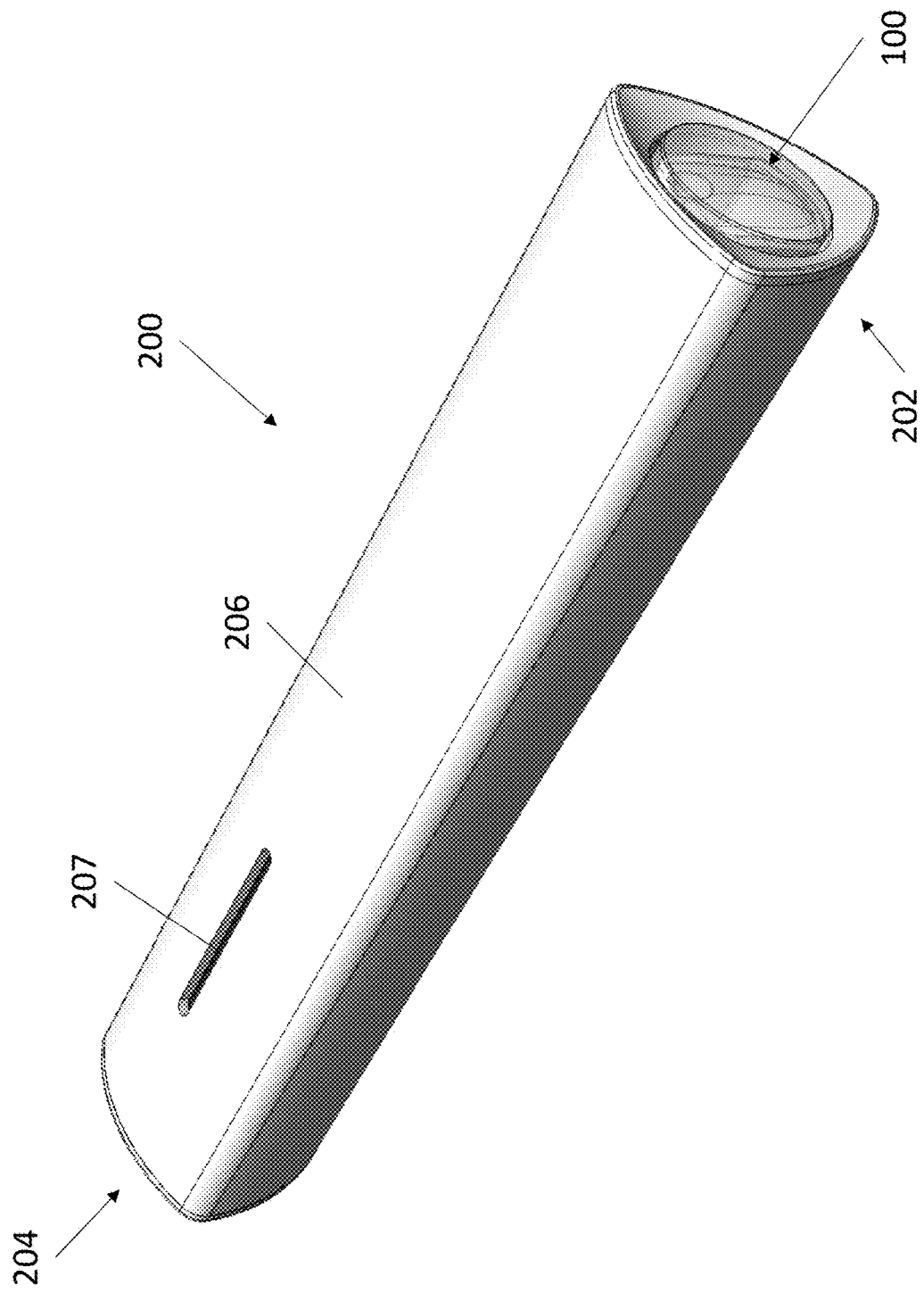
FIG. 11 depicts a perspective view of an exemplary triangular DPI with a DPI cartridge inserted.

Referring now to FIG. 11, an exemplary DPI casing 200 is depicted. DPI casing 200 has an anterior end 202 and a posterior end 204 and comprises casing 206. While casing 206 is depicted in FIG. 11 as having a substantially triangular cross section, it should be understood that casing 206 can comprise any suitably shaped cross section. DPI casing 200 accepts cartridge 100 at anterior end 202. In certain embodiments, fuel gauge window 207 is provided on casing 206 to indicate the amount of dry powder remaining in cartridge 100.

Figure 12A:
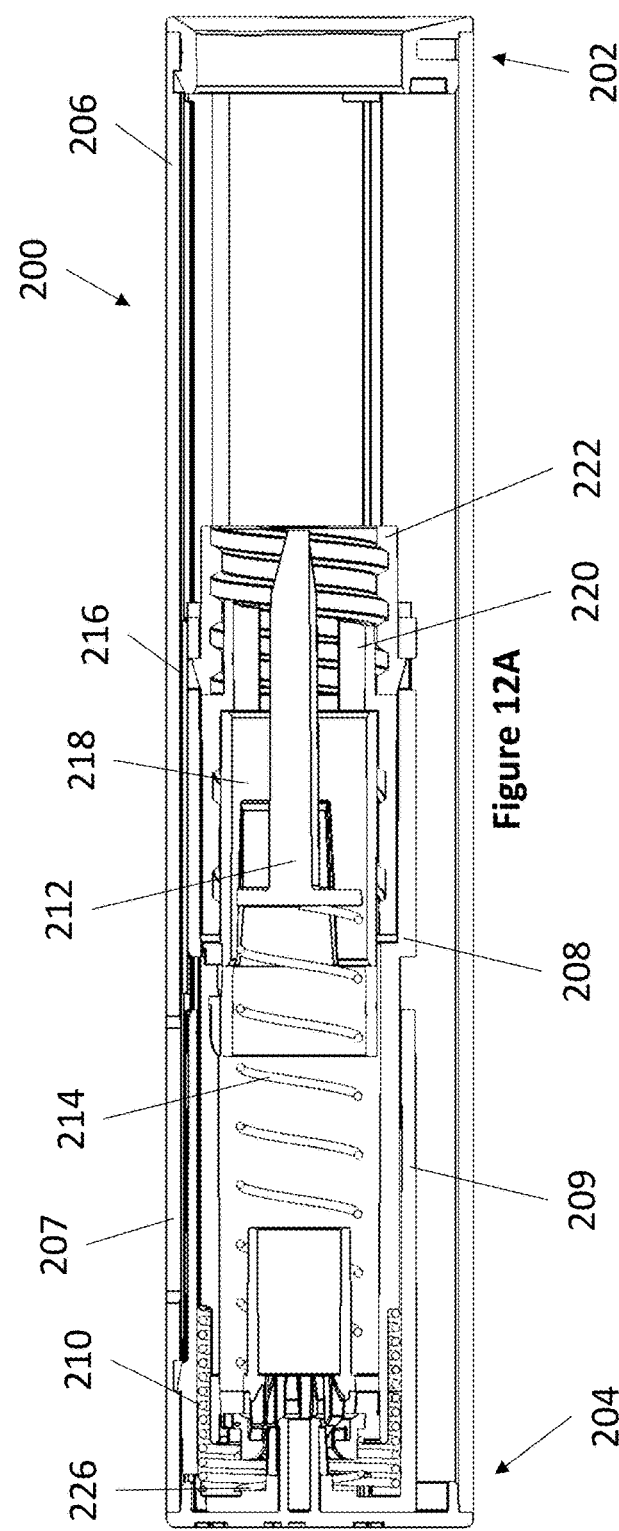
FIG. 12A and FIG. 12B depict wireframe cross sectional views of an exemplary triangular DPI from the left without a DPI cartridge (FIG. 12A) and with a DPI cartridge (FIG. 12B).
Figure 12B:
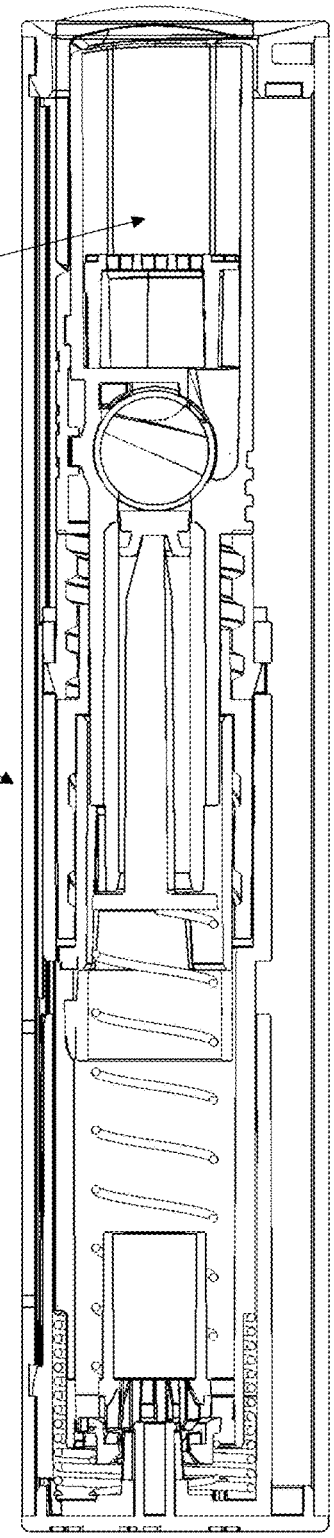

Referring now to FIG. 12A and FIG. 12B, the components of an exemplary DPI casing 200 are depicted. Starting at posterior end 204 DPI casing 200 comprises cam spring 226, shuttle spring 210, chassis 209, plunger spring 214, shuttle 208, plunger 212, enforcer 218, fuel gauge 216, sleeve 220, and shuttle cap 222.

Referring now to FIG. 13A, FIG. 13B, FIG. 14A, and FIG. 14B, shuttle 208 is now described. Shuttle 208 comprises a substantially hollow cylindrical shape having an open anterior end and a closed posterior end. Near the anterior end, shuttle 208 comprises shuttle cap slot 232 to secure shuttle cap 222, as described elsewhere herein. Near the posterior end, shuttle 208 comprises shuttle track 230, through which plunger spring retainer 228 is visible. At the posterior end, shuttle 208 comprises shuttle cam stopper 235 arranged at 90° intervals and shuttle cam mechanism 234, as described elsewhere herein. Tooth 236 is provided to engage sleeve 220, as described elsewhere herein. In certain embodiments, flex space 238 is provided a degree of flexibility to tooth 236.

Figure 15:
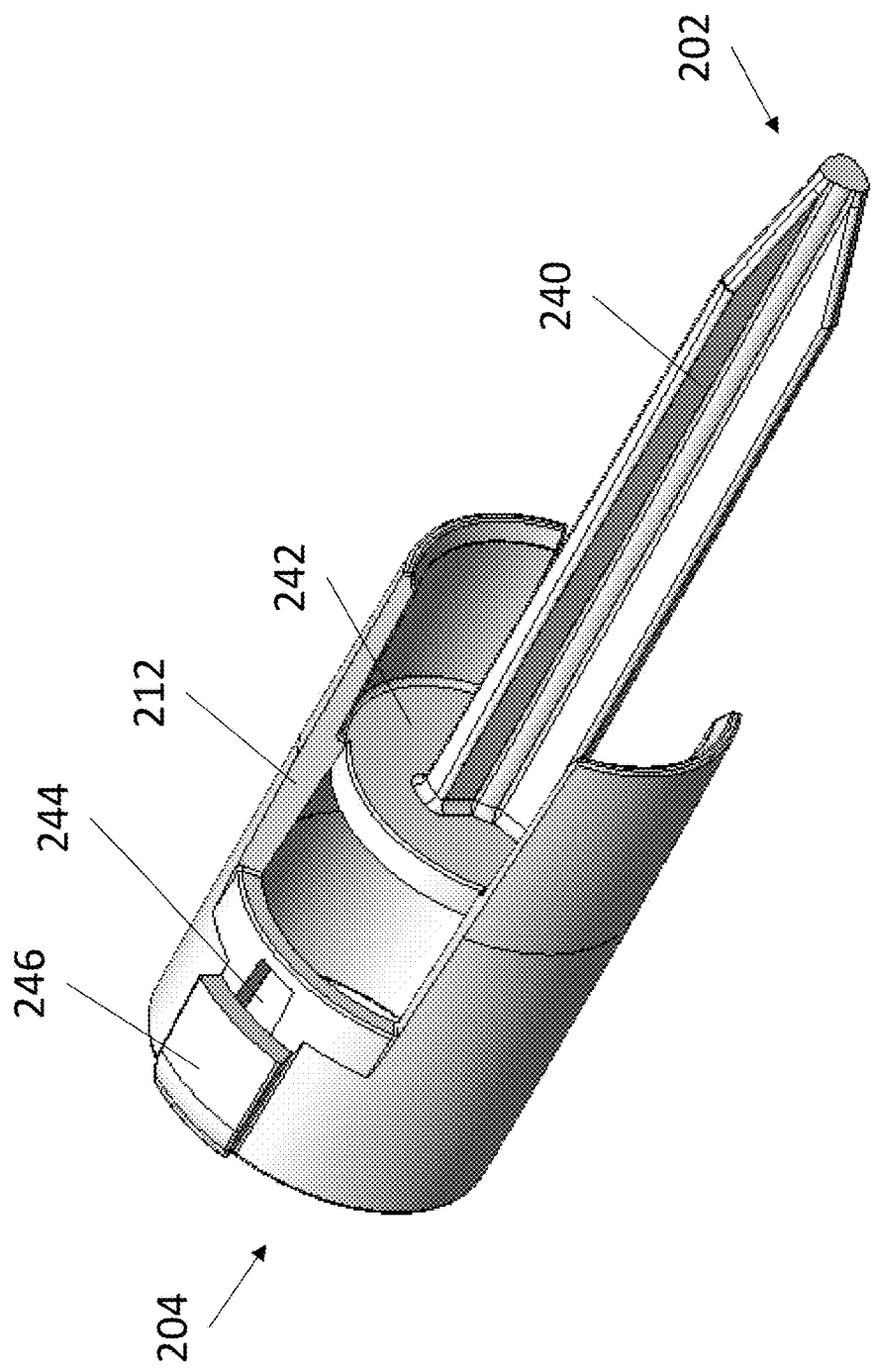
FIG. 15 depicts a perspective view of an exemplary triangular DPI plunger part from the front left.

Referring now to FIG. 15, plunger 212 is now described. Plunger 212 comprises a substantially hollow cylindrical body wherein a disc-shaped spring seat 242 is disposed within. Plunger tip 240 extends from spring seat 242 in an anterior direction. The exterior of plunger 212 comprises track slider 246 that engages shuttle track 230 of shuttle 208, such that plunger 212 and attached components slide linearly within shuttle 208 without rotation. In certain embodiments, plunger 212 further comprises fuel gauge slot 244 to secure fuel gauge 216, as described elsewhere herein.

Figure 16A:
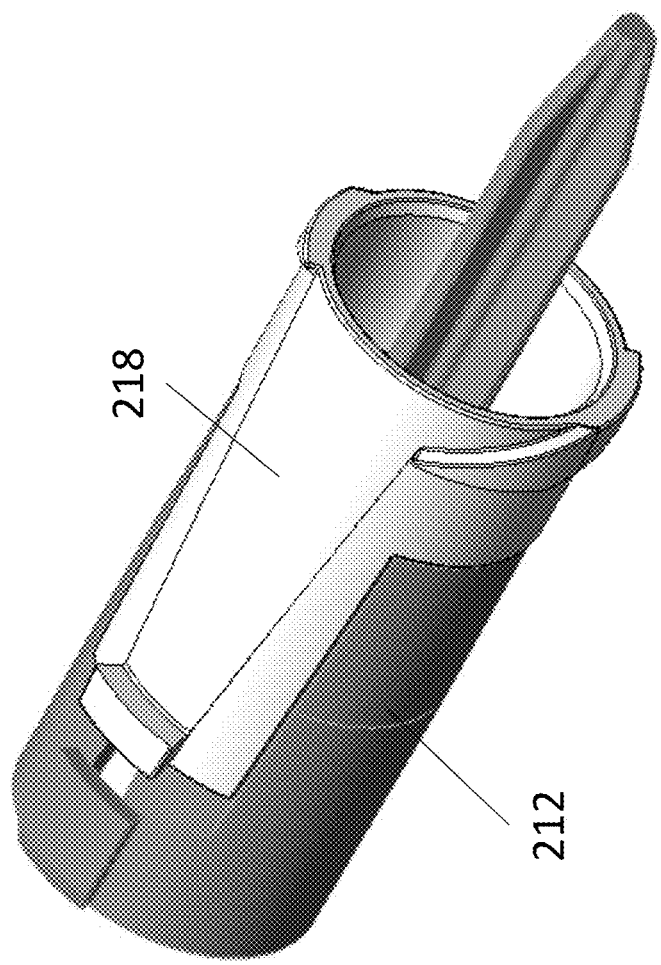
FIG. 16A and FIG. 16B depict front left perspective views of an exemplary triangular DPI enforcer part in isolation (FIG. 16A) and combined with a plunger part (shaded) (FIG. 16B).
Figure 16B:
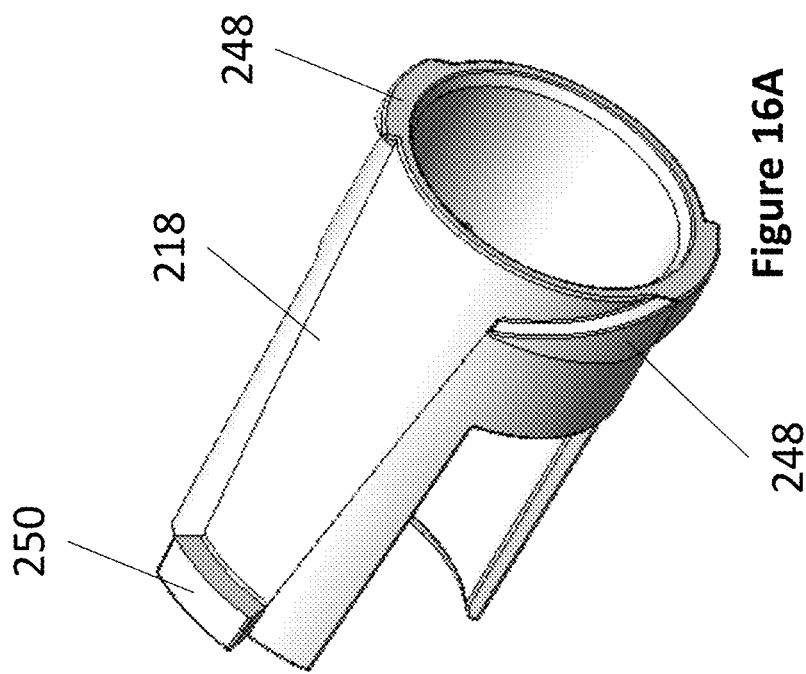
Figure 18A:
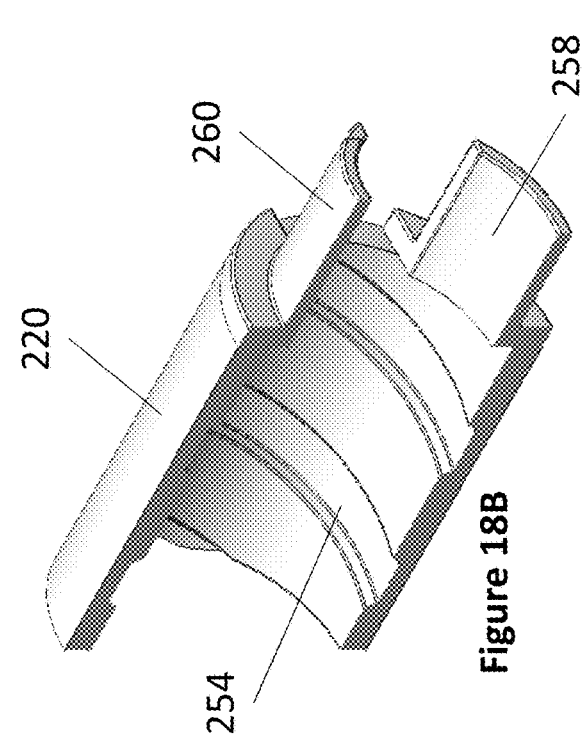
FIG. 18A through FIG. 18D depict perspective views of an exemplary triangular DPI sleeve part from the front left (FIG. 18A), front left cross sectional (FIG. 18B), from the right (FIG. 18C), and from the bottom (FIG. 18D).
Figure 18B:
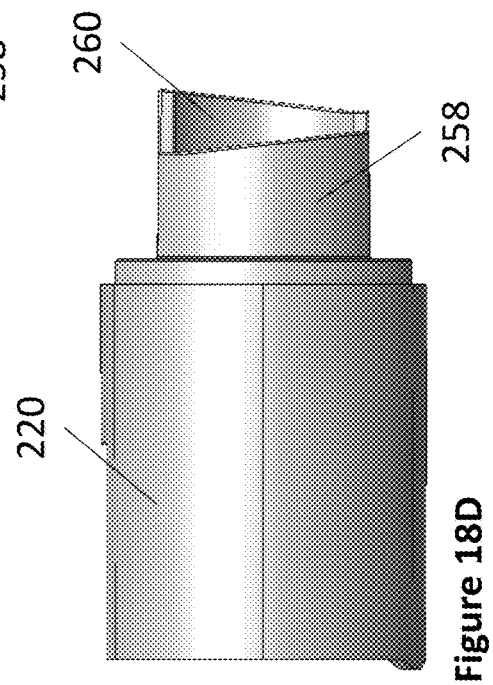
Figure 18C:
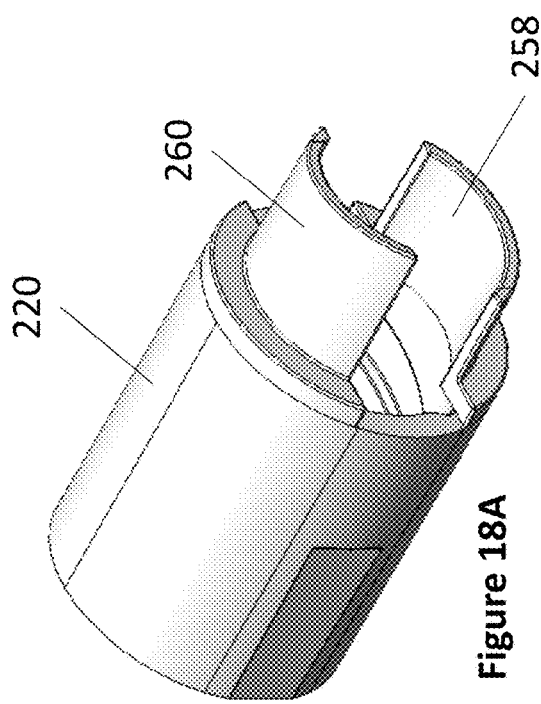
Figure 18D:
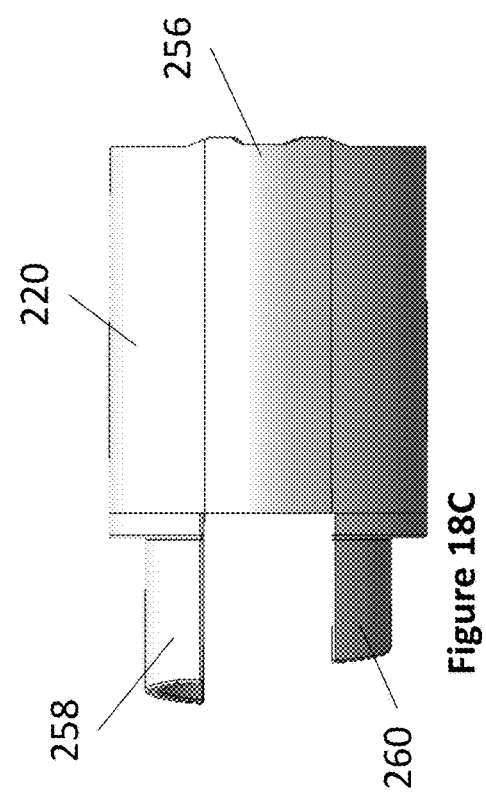

Referring now to FIG. 16A and FIG. 16B, enforcer 218 is now described. Enforcer 218 is shaped such that enforcer 218 forms a substantially continuous cylindrical surface when fitted with plunger 212. Enforcer 218 comprises threads 248 and spline 250 to prevent enforcer 218 from rotating within DPI casing 200.

Referring now to FIG. 17A and FIG. 17B, fuel gauge 216 is now described. In embodiments of DPI casing 200 featuring fuel gauge window 207, fuel gauge 216 is provided to indicate the amount of dry powder remaining in a cartridge 100 installed in DPI casing 200. Fuel gauge 216 comprises fuel gauge tab 252 that fits within fuel gauge slot 244 of plunger 252.

Figure 19:
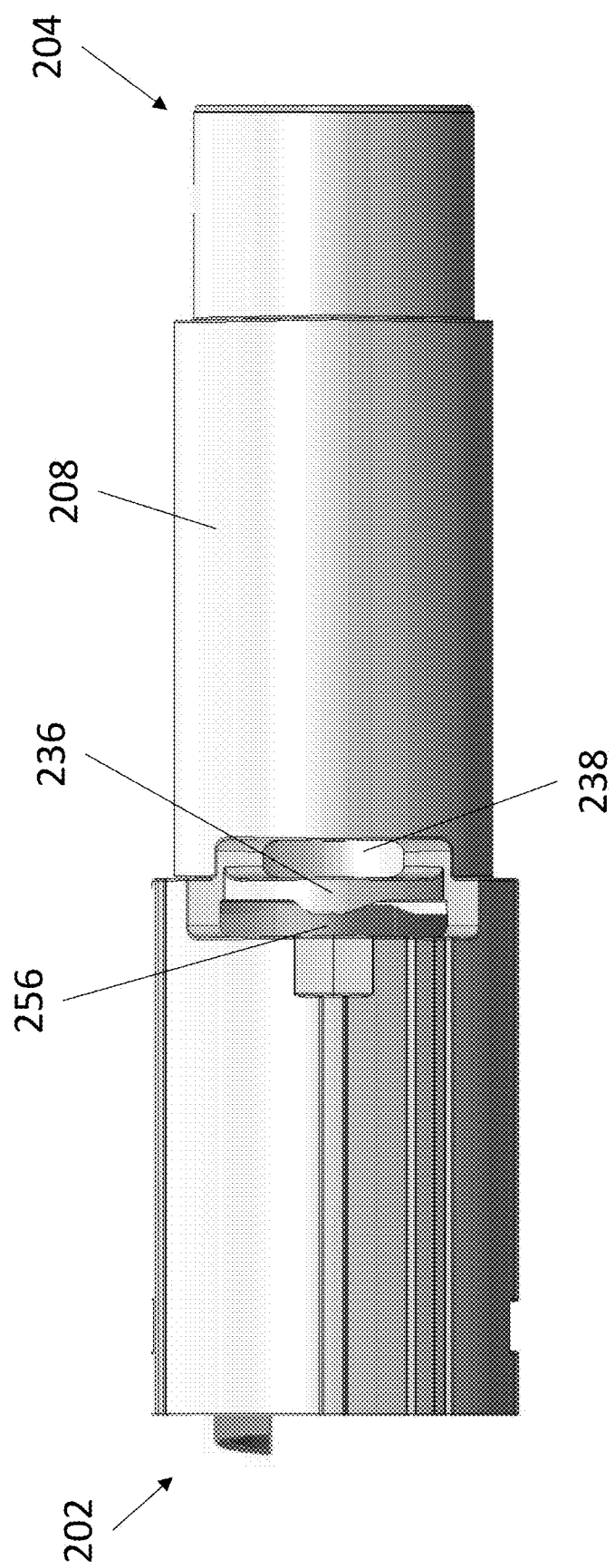
FIG. 19 depicts a right side view of an exemplary triangular DPI sleeve part (shaded) combined with a shuttle part.
Figure 20:
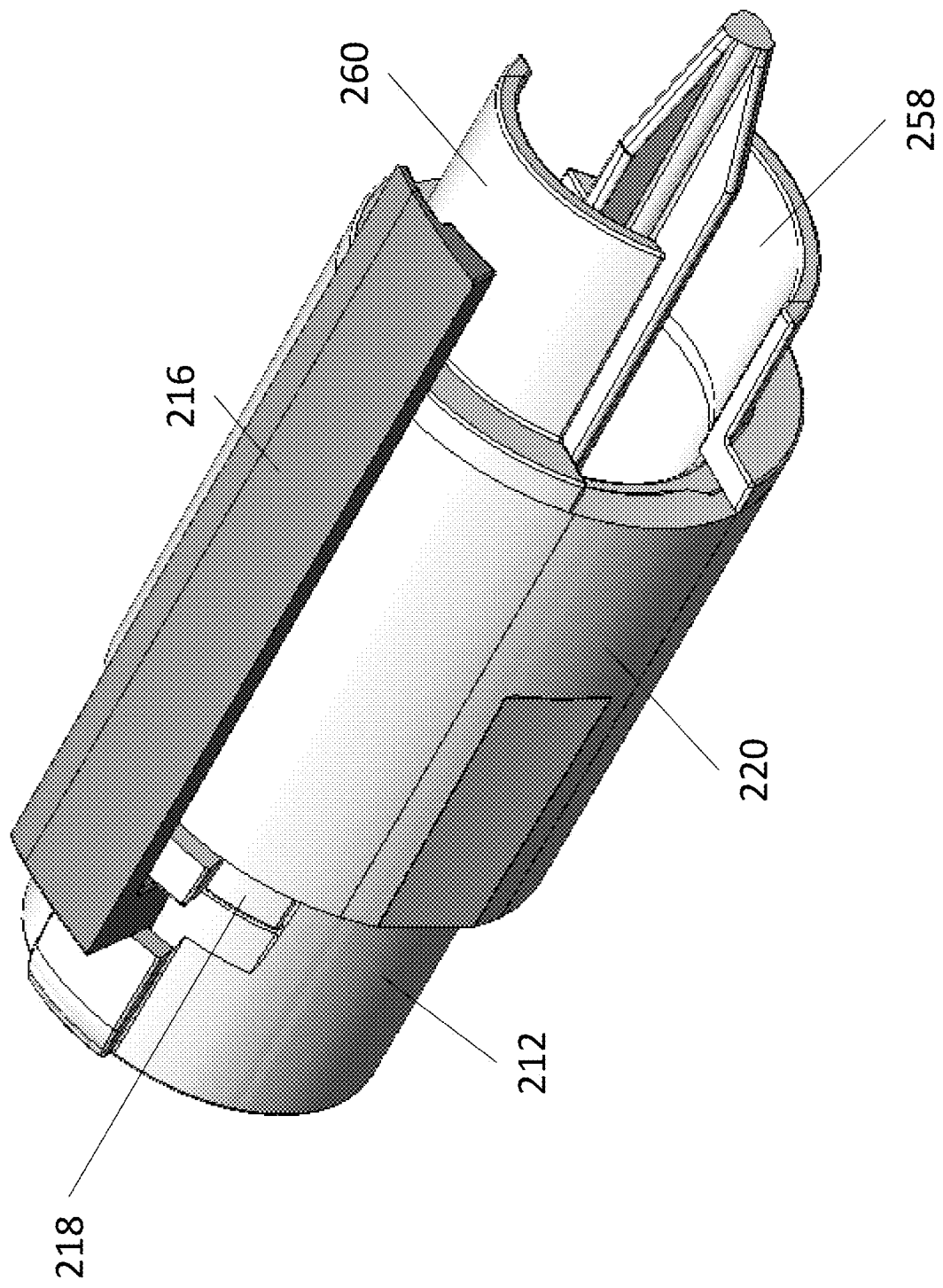
FIG. 20 depicts a front left perspective view of an exemplary triangular DPI sleeve part combined with the assembly depicted in FIG. 17A.

Referring now to FIG. 18A through FIG. 18D, sleeve 220 is now described. Sleeve 220 comprises a substantially hollow cylindrical shape open at both ends with internal thread 254 sized to engage thread 248 of enforcer 218, as described elsewhere herein. Sleeve 220 comprises short cuff 258 and long cuff 260, wherein short cuff 258 and long cuff 260 are actuated by thread 120 of cartridge 100 to rotate sleeve 220 within shuttle 208, as described elsewhere herein. Sleeve 220 comprises detent 256 at its posterior end to engage tooth 236 of shuttle 208 (also depicted in FIG. 19). The engagement between detent 256 and tooth 236 provides a tactile locking and unlocking feature to the rotation of sleeve 220 within shuttle 208, preventing the mechanism from spontaneously rotating under the influence of spring loads on the threads. Referring now to FIG. 20, sleeve 220 is depicted in combination with plunger 212, enforcer 218, and fuel gauge 216.

Figure 22A:
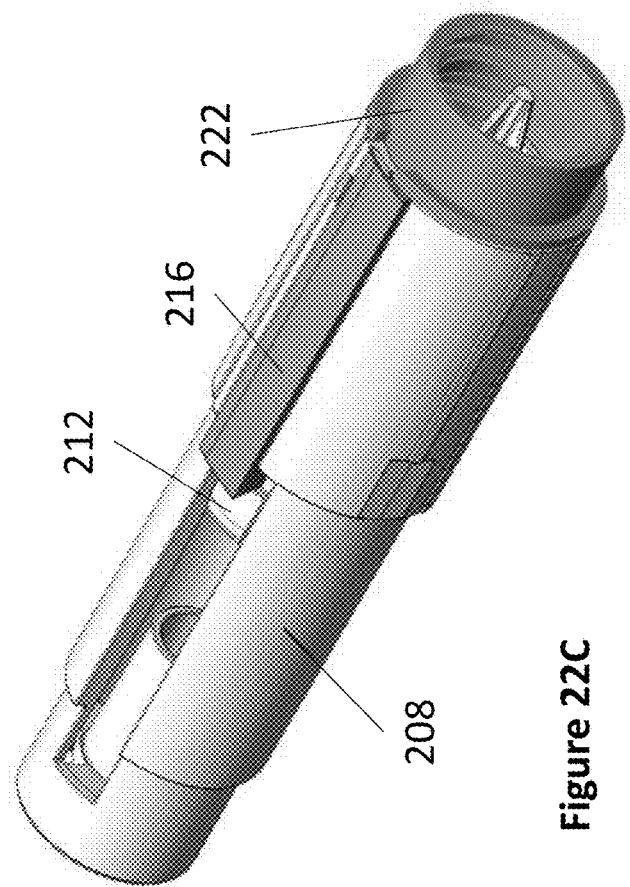
FIG. 22A through FIG. 22C depict a front left perspective view (FIG. 22A) and an angled front view (FIG. 22B) of an exemplary triangular DPI shuttle cap part combined with the assembly depicted in FIG. 20 and combined with a shuttle part (FIG. 22C).
Figure 22B:
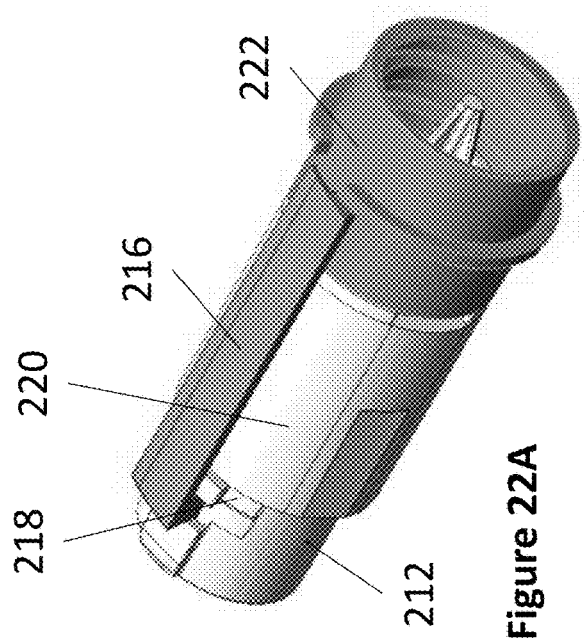
Figure 22C:
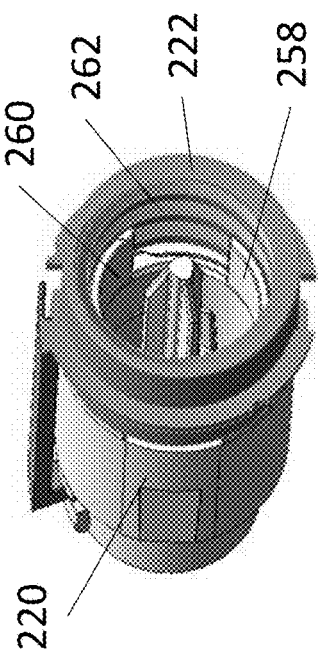

Referring now to FIG. 21A and FIG. 21B, shuttle cap 222 is now described. Shuttle cap 222 comprises a substantially ring shape with internal thread 262 sized to engage thread 120 of cartridge 100. Shuttle cap 222 further comprises shuttle cap tabs 264 to engage shuttle cap slots 232 of shuttle 208. Referring now to FIG. 22A, shuttle cap 222 (shaded) is depicted in combination with plunger 212, enforcer 218, fuel gauge 216 (shaded), and sleeve 220. Referring now to FIG. 22B, short cuff 258 and long cuff 260 of sleeve 220 lie flush against the inner surface of shuttle cap 222, just above internal thread 262. Referring now to FIG. 22C, the assembly of FIG. 22A is depicted in combination with shuttle 208.

Figures 23A, 23B, 23C:
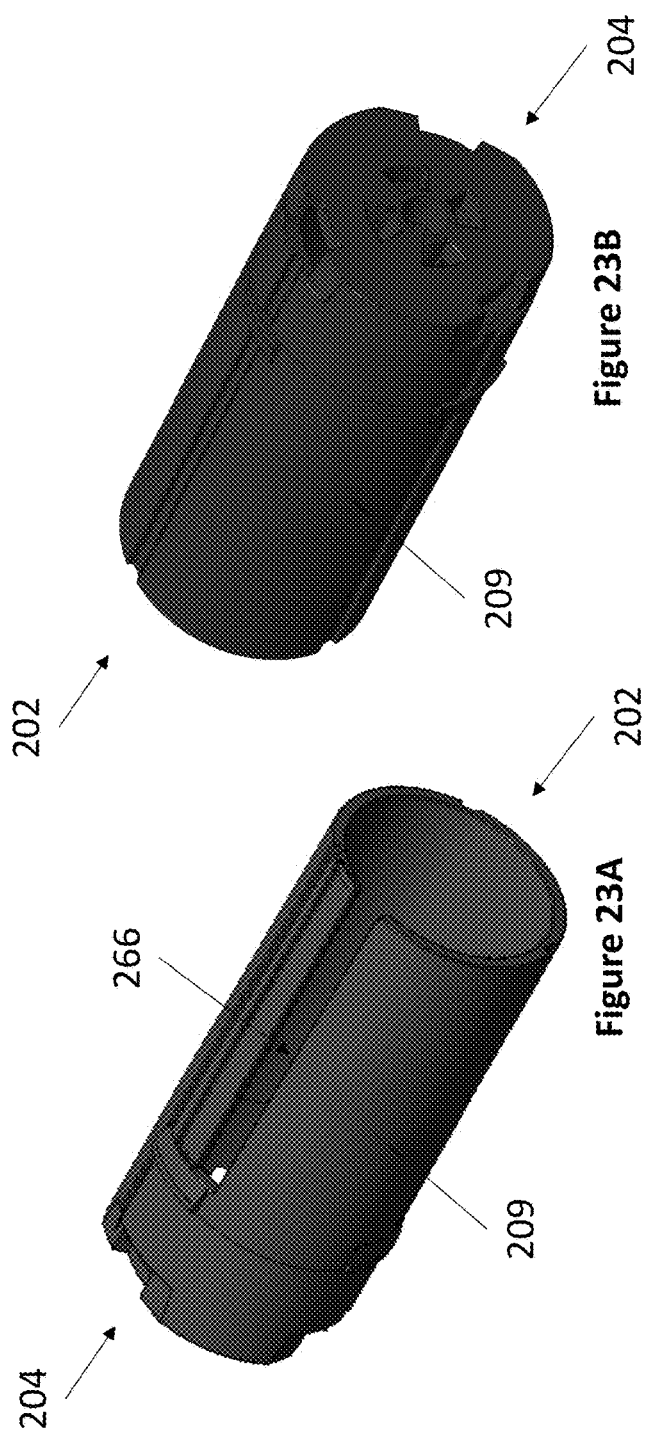
FIG. 23A through FIG. 23C depict various views of an exemplary triangular DPI chassis part from the front left (FIG. 23A), from the back right (FIG. 23B), and front left cutaway view (FIG. 23C).
Figure 24:
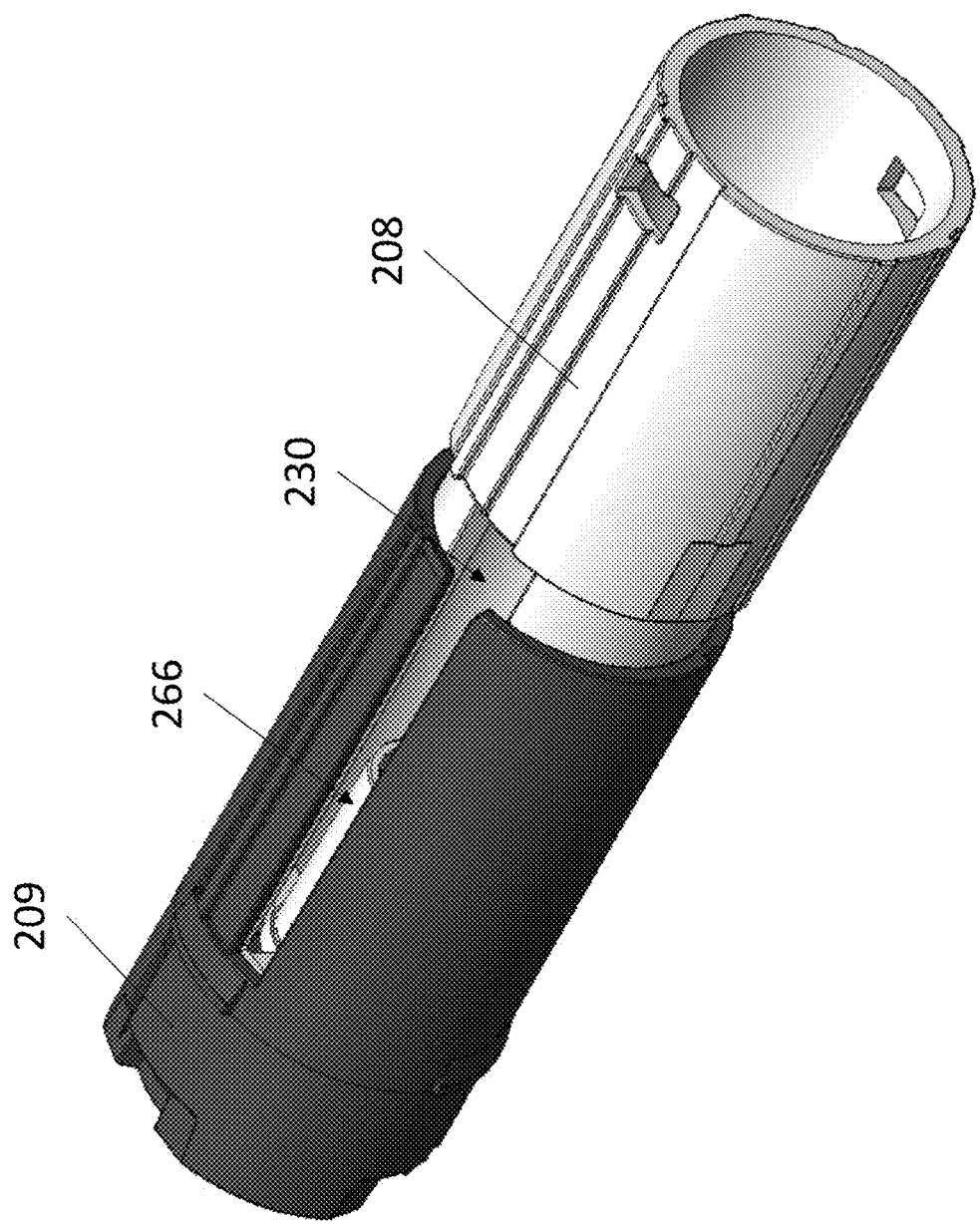
FIG. 24 depicts a front left view of an exemplary triangular DPI chassis part combined with a shuttle part.

Referring now to FIG. 23A through FIG. 23C, chassis 209 is now described. Chassis 209 comprises a substantially hollow cylindrical shape having an open anterior end and a closed posterior end. Chassis 209 comprises chassis track 266 along its exterior in alignment with shuttle track 230 (as shown in FIG. 24). Chassis 209 further comprises chassis cam mechanism 268 at its interior posterior end.

Figures 25A, 25B:
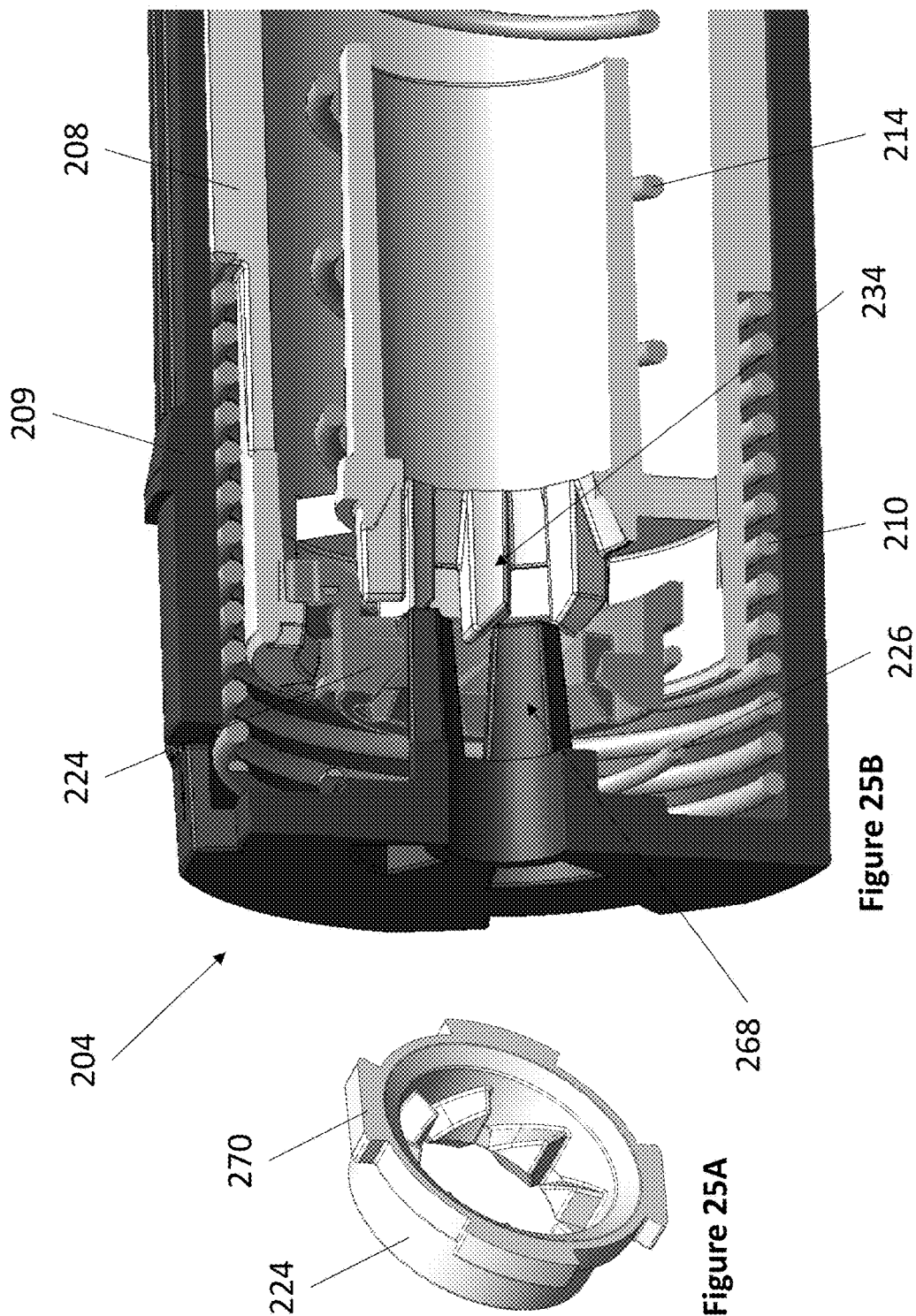
FIG. 25A and FIG. 25B depict various views of an exemplary triangular DPI rotary lock part in isolation (FIG. 25A) and combined (shaded) with a chassis part, a shuttle part, and a variety of springs.

Referring now to FIGS. 25A and 25B, rotary lock 224 is now described. Rotary lock 224 comprises a substantially ring shape having a series of teeth along its interior and rotary lock stoppers 270 along its exterior arranged at 90° intervals. In FIG. 25B, the interaction between the teeth of chassis cam mechanism 268, rotary lock 224 (shaded), and shuttle cam mechanism 234 is depicted, wherein chassis cam mechanism 268 and shuttle cam mechanism 234 work in tandem to rotate rotary lock 224 in steps, and wherein the rotation of rotary lock 224 engages and disengages rotary lock stoppers 270 with shuttle cam stopper 235 to lock and unlock shuttle 208.

Referring now to FIG. 26A through FIG. 26D, the mechanism of rotating rotary lock 224 (shaded) to lock and unlock shuttle 208 is depicted. The mechanism is similar to the function of a retractable pen cam mechanism. For clarity purposes, portions of chassis 209 and rotary lock 224 are cut away. Beginning with FIG. 26A, shuttle 208 is in a locked position due to shuttle cam stopper 235 engaging rotary lock stopper 270, preventing anterior movement in shuttle 208. Cam spring 226 provides a spring force between chassis 209 and rotary lock 224 to maintain rotary lock 224 in an anterior position, and shuttle spring 210 provides a spring force between chassis 209 and shuttle 208 to maintain shuttle 208 in an anterior position (not pictured). Rotary lock 224 is unable to rotate by engaging the teeth of chassis cam mechanism 268. In FIG. 26B, shuttle 208 is shifted in a posterior direction, whereupon the angled teeth of shuttle cam mechanism 234 shifts rotary lock 224 in a posterior direction to clear rotary lock 224 from the teeth of chassis cam mechanism 268 and freeing rotary lock 224 to rotation. The angled teeth of shuttle cam mechanism 234 then initiates the rotation of rotary lock 224 and the repositioning of rotary lock stoppers 270. In FIG. 26C, as shuttle 208 is shifted in an anterior direction by shuttle spring 210, rotary lock 224 is shifted in an anterior direction by cam spring 226. The rotation step of rotary lock 224 is completed by its engagement with the angled teeth of chassis cam mechanism 268, whereupon rotary lock stoppers 270 are fully disengaged from shuttle cam stoppers 235, enabling shuttle spring 210 to fully push shuttle 208 in an anterior direction. In FIG. 26D, shuttle 208 is shifted in a posterior direction, whereupon the angled teeth of shuttle cam mechanism 234 shifts rotary lock 224 in a posterior direction to clear rotary lock 224 from the teeth of chassis cam mechanism 268 and freeing rotary lock 224 to rotation once again. The angled teeth of shuttle cam mechanism 234 initiates the rotation of rotary lock 224 and the repositioning of rotary lock stoppers 270. As shuttle 208 is shifted in an anterior direction by shuttle spring 210, rotary lock 224 is shifted in an anterior direction by cam spring 226 once again. The rotation step of rotary lock 224 is completed by its engagement with the angled teeth of chassis cam mechanism 268, whereupon rotary lock stoppers 270 fully engage shuttle cam stoppers 235, locking further movement of shuttle 208 in an anterior direction as depicted in FIG. 26A.

Referring now to FIG. 27A through FIG. 27D, the mechanism of loading an exemplary cartridge 100 into an exemplary DPI casing 200 is depicted. Beginning with FIG. 27A, without a cartridge inserted, shuttle spring 210 (not pictured) biases shuttle 208 against the anterior end of DPI casing 200, while plunger spring 214 (not pictured) biases plunger 212 against enforcer 218. In this manner, enforcer 218 prevents plunger 212 from protruding out of the anterior end of DPI casing 200, permitting a user to insert a cartridge 100 without having to overcome the plunger spring load. In FIG. 27B, cartridge 100 is inserted into DPI casing 200 by engaging thread 120 of cartridge 100 into internal thread 262 of shuttle cap 222, which aligns piston 109 of reservoir 108 with plunger tip 240. In FIG. 27C, cartridge 100 is continually screwed in until thread 120 catches long cuff 260 of sleeve 220, whereupon sleeve 220 rotates in place in shuttle 208 with the screwing in motion of cartridge 100. As sleeve 220 rotates, internal thread 254 of sleeve 220 engages thread 248 of enforcer 218, pulling enforcer 218 in an anterior direction. With cartridge 100 fully screwed in, enforcer 218 is in an anterior position, detent 256 of sleeve 220 has engaged tooth 236 of shuttle 208, and plunger 212 has been pushed to a posterior position within shuttle 208. In FIG. 27D, cartridge 100 is pushed fully into DPI casing 200, whereupon shuttle cam mechanism 234 engages rotary lock 224 to hold shuttle 208 and cartridge 100 in place.

Referring now to FIG. 28A through 28D, the mechanism of dispensing and advancing doses of dry powder in an exemplary cartridge 100 using an exemplary DPI casing 200 is depicted. From FIG. 27D, cartridge 100 and shuttle 208 are moved in a posterior direction to disengage shuttle cam mechanism 234 from rotary lock 224, whereupon shuttle spring 210 (not pictured) moves cartridge 100 and shuttle 208 to an anterior position in FIG. 28A. Cap 110 of cartridge 100 thereby has clearance to be actuated fully open, delivering a dose of dry powder as depicted in FIG. 10A through FIG. 10F. In FIG. 28B, cap 110 is closed, actuating drum 114 and rotating an empty powder dose aperture 136 to face powder entry port 133. Plunger spring 214 (not pictured) then advances plunger 212 in an anterior direction, pushing piston 109 in an anterior direction to maintain compression on the amount of dry powder within reservoir 108 and to fill the empty space of powder dose aperture 136. Anterior movement of plunger 212 is corresponded by anterior movement of fuel gauge 216. When cartridge 100 and shuttle 208 are pushed fully into DPI casing 200, the position of fuel gauge 216 is visible through fuel gauge window 207, indicating the relative amount of dry powder remaining. FIG. 28C depicts a half full cartridge 100, with corresponding position of piston 109, plunger 212, and fuel gauge 216. FIG. 28D depicts an empty cartridge 100, with corresponding position of piston 109, plunger 212, and fuel gauge 216. Cartridge 100 may then be removed by reversing the steps depicted in FIG. 27A through FIG. 27D.

Figures 29A, 29B:
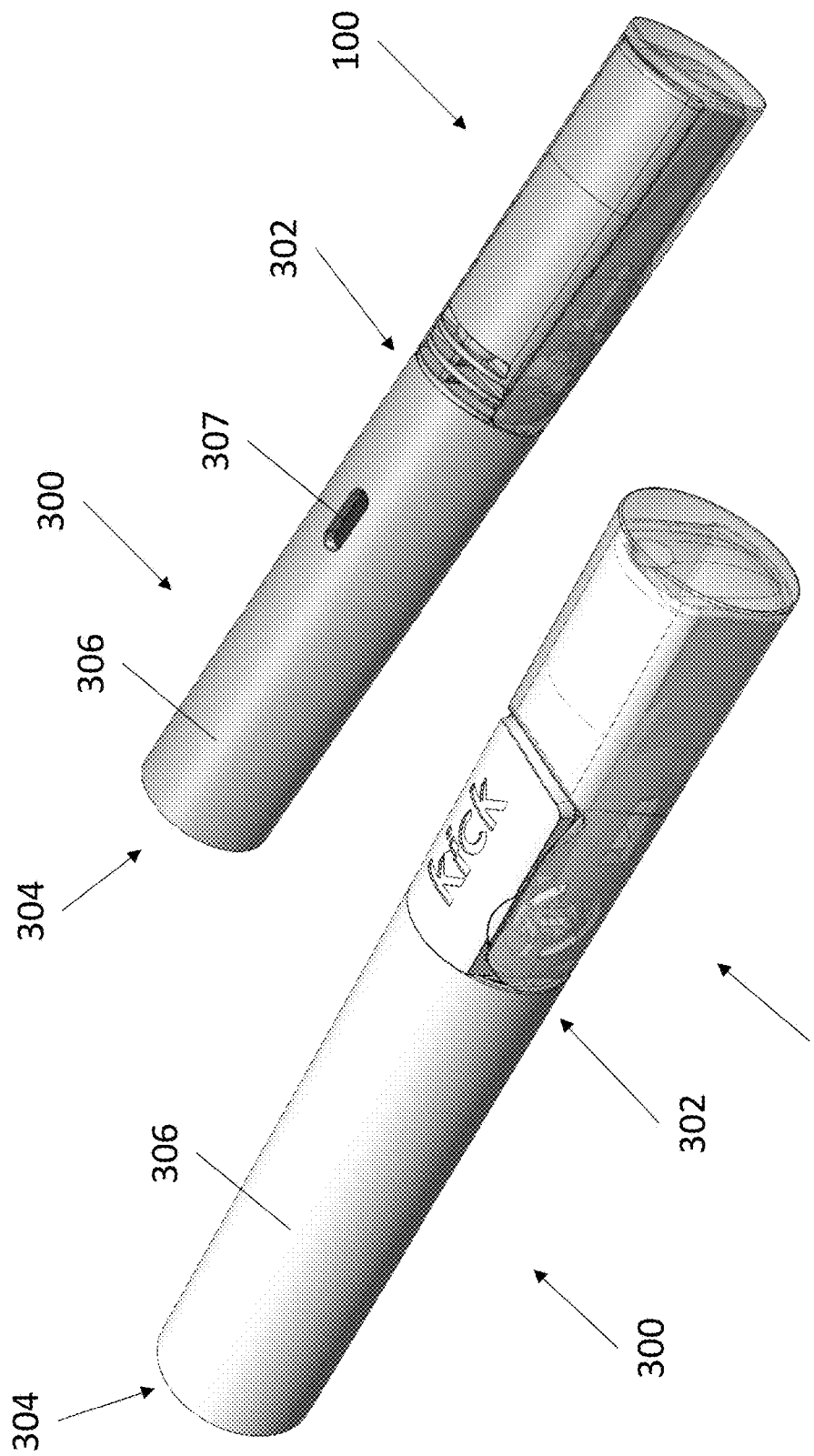
FIG. 29A and FIG. 29B depict perspective views of an exemplary micro DPI from the front left top (FIG. 29A) and from the front right bottom (FIG. 29B).

Referring now to FIG. 29A and FIG. 29B, an exemplary micro DPI casing 300 is depicted. DPI casing 300 has an anterior end 302 and a posterior end 304 and comprises casing 306. While casing 306 is depicted as having a substantially circular cross section, it should be understood that casing 306 can comprise any suitably shaped cross section. DPI casing 300 accepts cartridge 100 at anterior end 302. In certain embodiments, fuel gauge window 307 is provided on casing 306 to indicate the amount of dry powder remaining in cartridge 100.

Referring now to FIG. 30A and FIG. 30B, the components of an exemplary DPI casing 300 are depicted. Starting at posterior end 304 DPI casing 300 comprises plunger spring 310 and plunger 308.

Figure 31:
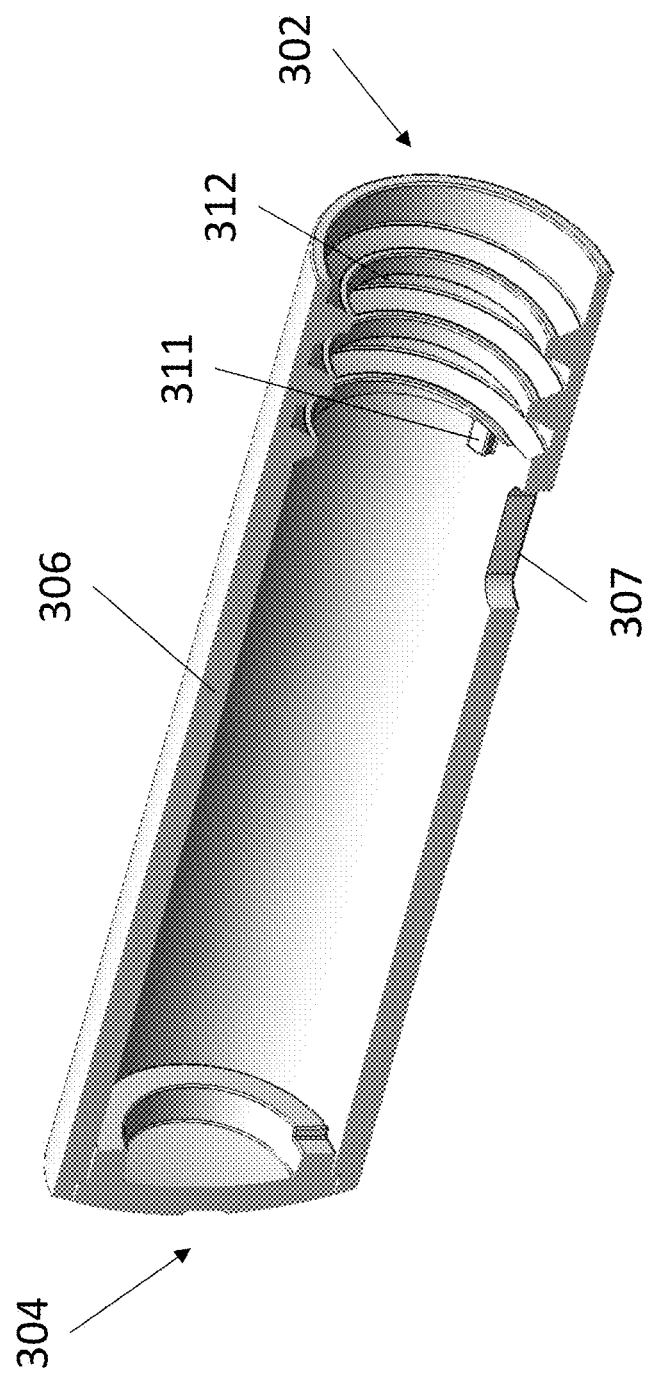
FIG. 31 depicts a cross sectional front left perspective view of an exemplary micro DPI casing.

Referring now to FIG. 31, casing 306 is now described. Casing 306 comprises a substantially hollow cylindrical shape having an open anterior end and a closed posterior end. Casing 306 further comprises internal thread 312 at its anterior end. Casing 306 comprises one or more plunger stoppers 311 immediately posterior to internal thread 312.

Figure 32A:
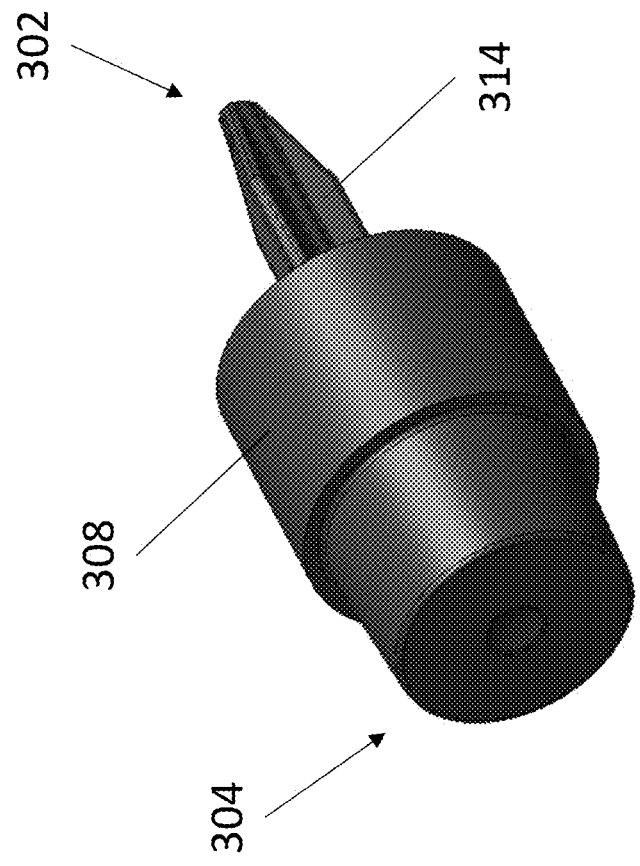
FIG. 32A and FIG. 32B depict perspective views of an exemplary micro DPI plunger part from the front left (FIG. 32A) and the rear left (FIG. 32B).
Figure 32B:
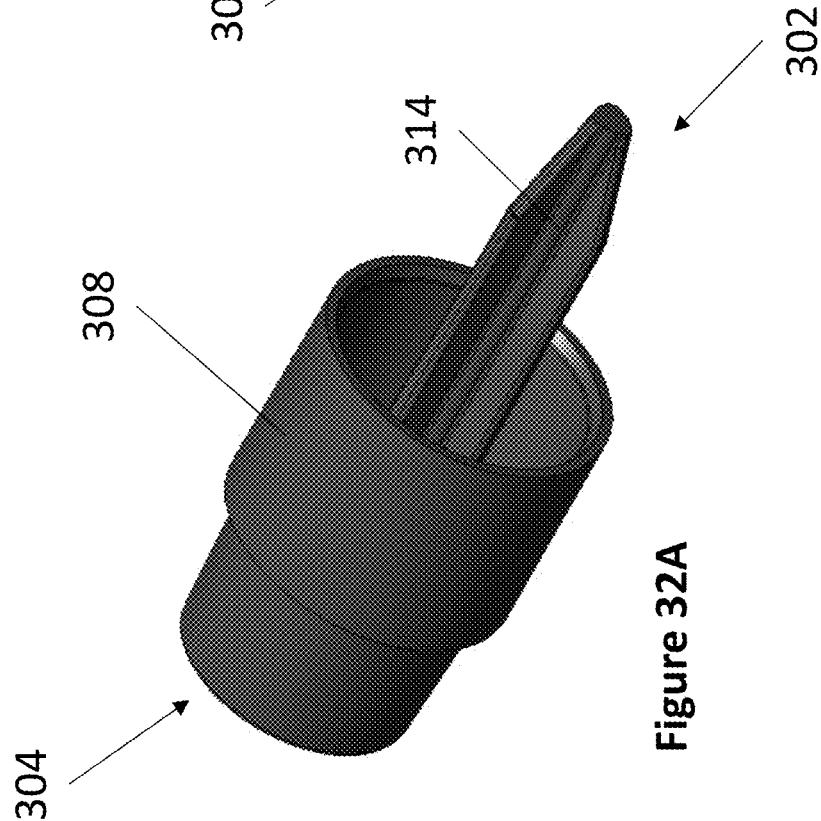

Referring now to FIG. 32A and FIG. 32B, plunger 308 is now described. Plunger 308 comprises a substantially hollow cylindrical shape having an open anterior end and a closed posterior end. Plunger 308 further comprises plunger tip 314 extending from the closed posterior end. Plunger 308 comprises a slightly narrower diameter at its posterior end to accommodate the diameter of plunger spring 310.

Figure 33:
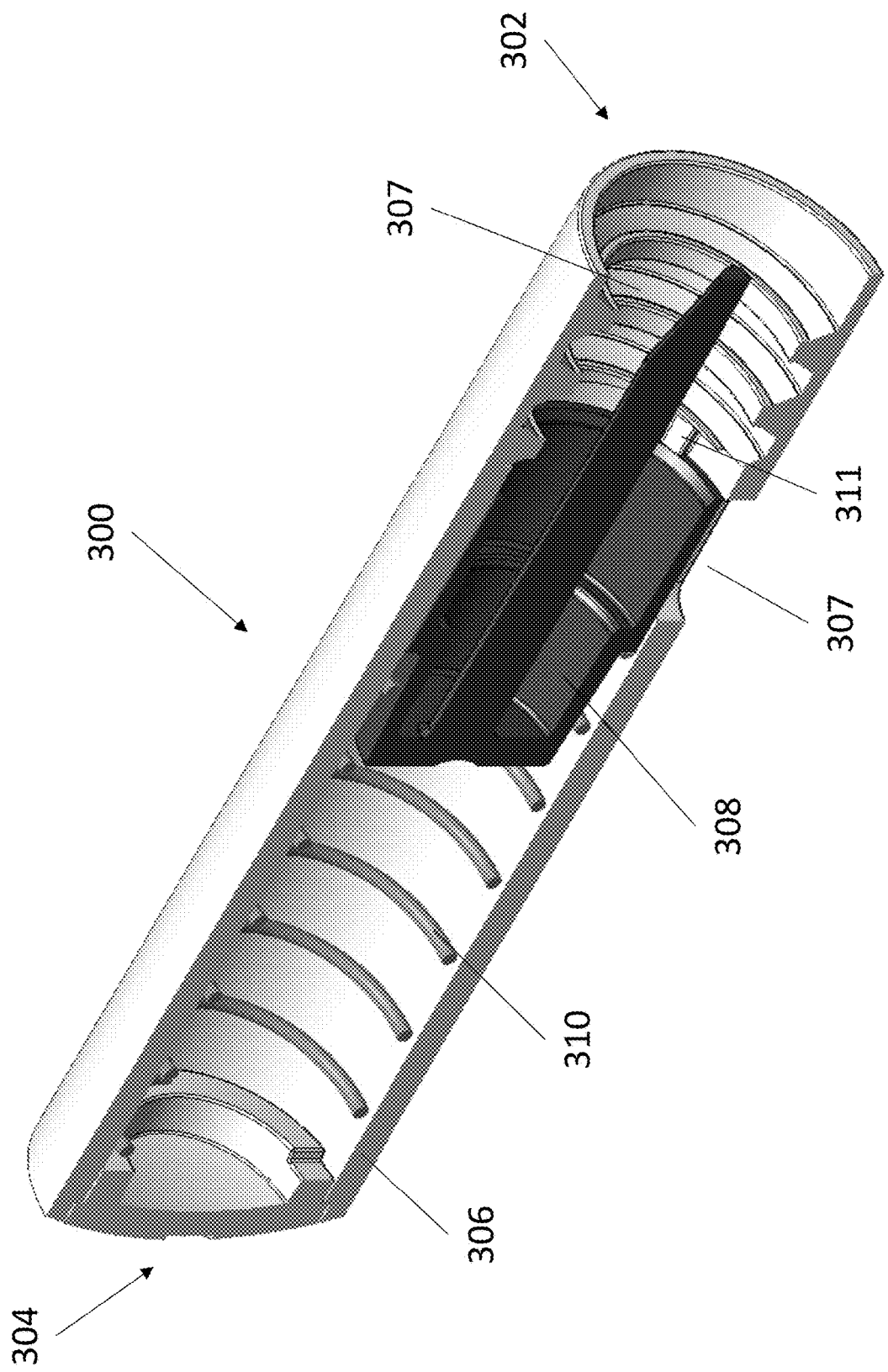
FIG. 33 depicts a cross sectional front left perspective view of an exemplary micro DPI.

Referring now to FIG. 33, the mechanism of dispensing dry powder using DPI casing 300 is now described. DPI casing 300, depicted without a cartridge in FIG. 33, positions plunger 308 in an anterior position. Plunger 308 maintained in the anterior position by plunger spring 310 and is prevented from exiting casing 306 by plunger stoppers 311. Cartridge 100 is inserted by aligning plunger tip 314 with piston 109 of cartridge 100, then screwing thread 120 of cartridge 100 into internal thread 312 of casing 306 (not pictured). As cartridge 100 is screwed in, plunger 308 is pushed to a posterior position. Cartridge 100 attaches to DPI casing 300 in an exposed manner (FIG. 29A), such that DPI casing 300 may dispense doses of dry powder simply by actuating cap 110 as depicted in FIG. 10A through FIG. 10F. As cap 110 is closed after delivery of each dose, drum 114 is actuated, rotating an empty powder dose aperture 136 to face powder entry port 133. Plunger spring 310 then advances plunger 308 in an anterior direction, pushing piston 109 in an anterior direction to maintain compression on the amount of dry powder within reservoir 108 and to fill the empty space of powder dose aperture 136. As the amount of dry powder in cartridge 100 is diminished, plunger 308 advances in an anterior direction and approaches fuel gauge window 307, whereupon the coloring of plunger 308 becomes visible through fuel gauge window 307, indicating low dry powder supply. Full depletion of dry powder in cartridge 100 is indicated by plunger 308 completely occluding fuel gauge window 307.

Methods of Making

The several components disclosed herein can be constructed from any suitable material, such as a plastic or metal. In certain embodiments, certain components may comprise additional materials where noted.

The devices of the present invention can be made using any suitable method known in the art. The method of making may vary depending on the materials used. For example, devices substantially comprising a metal may be milled from a larger block of metal or may be cast from molten metal. Likewise, devices substantially comprising a plastic or polymer may be milled from a larger block or injection molded. In some embodiments, the devices may be made using 3D printing or other additive manufacturing techniques commonly used in the art.

Dry Powder Inhalation System

The present invention also relates to dry powder inhalation systems. The systems of the present invention comprise the devices described herein for use in dispensing dry powder. For example, in certain embodiments, the systems comprise at least one dry powder inhaler casing. In other embodiments, the systems comprise at least one dry powder inhaler cartridge. In other embodiments, the systems comprise at least one amount of dry powder. In certain embodiments, the at least one dry powder inhaler casing, the at least one dry powder inhaler cartridge, and the at least one amount of dry powder of the systems are interchangeable. In some embodiments, the at least one cartridge is preloaded with an amount of dry powder. In other embodiments, the at least one cartridge is provided with an empty powder reservoir, whereupon a powder may be selected and loaded.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A dry powder cartridge device, comprising:
   an elongate body having an anterior end and a posterior end;
   a delivery lumen positioned at the anterior end of the body;
   a powder reservoir positioned at the posterior end of the body;
   a powder metering drum assembly positioned anterior to the powder reservoir, the powder metering drum assembly comprising a cylindrical outer drum and a cylindrical inner drum insert having a curved exterior, wherein the cylindrical outer drum is rotatable along the curved exterior of the inner drum insert; and
   an actuating cap positioned at the anterior end of the body mechanically engaged to the powder metering drum;
   wherein an amount of powder within the powder reservoir is advanced towards the powder metering drum by a piston.

2. The device of claim 1, wherein the elongate body comprises at least one air inlet fluidly connected to the powder metering drum assembly.

3. The device of claim 1, wherein the delivery lumen comprises a side air inlet to introduce a vortex airflow into the delivery lumen.

4. The device of claim 1, wherein the delivery lumen comprises a mesh to break apart powder agglomerates and vortex airflow.

5. The device of claim 4, wherein a flow of air introduced through the delivery lumen at a rate of 20 to 40 L/min is sufficient to break apart powder agglomerates and vortex airflow.

6. The device of claim 1, wherein the cylindrical outer drum comprises a powder dose aperture and an air aperture positioned opposite from the powder dose aperture.

7. The device of claim 6, wherein the inner drum insert has a delivery air inlet on the curved exterior facing upwards, a delivery air outlet on the curved exterior facing downwards opposite from the delivery air inlet, and a lumen passing through the inner drum insert connecting the delivery air inlet and the delivery air outlet.

8. The device of claim 7, wherein the actuating cap rotates the outer drum about the curved exterior of the inner drum insert.

9. The device of claim 8, wherein rotating the outer drum to face the powder dose aperture towards the powder reservoir deposits a dose of dry powder from the powder reservoir into a space bordered by the powder dose aperture and the curved exterior of the inner drum insert.

10. The device of claim 8, wherein rotating the outer drum to align the powder dose aperture with the delivery air outlet simultaneously aligns the air aperture with the delivery air inlet.

11. The device of claim 10, wherein the air aperture does not begin to overlap with the delivery air inlet until the powder dose aperture completely disengages from the powder reservoir.

12. The device of claim 10, wherein the alignment of the powder dose aperture with the delivery air outlet and the air aperture with the delivery air inlet creates a fluid communication between the at least one air inlet of the elongate body, the lumen of the inner drum insert, and the delivery lumen.

13. A dry powder inhaler casing device, comprising:
a casing having a lumen throughout, an open anterior end, and a closed posterior end;
a plunger within the casing lumen; and
a plunger spring within the casing lumen positioned between the plunger and the closed posterior end of the casing;
wherein the open anterior end of the casing is sized to accept the cartridge of claim 1.

14. The device of claim 13, wherein the plunger spring presses the plunger against the piston of the cartridge, such that the piston is advanced in an anterior direction as the powder reservoir is depleted.

15. The device of claim 13, wherein the casing comprises a window through which a portion of the plunger is visible, such that the advancement and position of the plunger can be determined through the window.

16. A dry powder inhalation system, comprising:
a dry powder inhaler casing device;
at least one cartridge insertable in the dry powder inhaler casing device, the cartridge comprising:
an elongate body having an anterior end and a posterior end;
a powder reservoir disposed within the elongate body; and
a powder metering drum assembly disposed anterior to the powder reservoir, the powder metering drum assembly comprising a cylindrical outer drum and a cylindrical inner drum insert; and
an actuating cap positioned at the anterior end of the body mechanically engaged to the powder metering drum assembly and constructed to rotate the cylindrical outer drum; and
at least one amount of powder.

17. The system of claim 16, wherein the at least one amount of powder is preloaded into the at least one cartridge powder reservoir.

18. The system of claim 16, wherein the at least one amount of powder is manually loaded into the at least one cartridge powder reservoir.

19. The system of claim 16, wherein the at least one powder inhaler casing and the at least one cartridge are interchangeable.

20. The system of claim 16, wherein the at least one cartridge is disposable.

* * * * *